US011605185B2

(12) United States Patent
Mariampillai et al.

(10) Patent No.: US 11,605,185 B2
(45) Date of Patent: *Mar. 14, 2023

(54) SYSTEM AND METHOD FOR GENERATING PARTIAL SURFACE FROM VOLUMETRIC DATA FOR REGISTRATION TO SURFACE TOPOLOGY IMAGE DATA

(71) Applicant: 7D SURGICAL INC., Toronto (CA)

(72) Inventors: Adrian Linus Dinesh Mariampillai, Toronto (CA); Peter Siegler, Toronto (CA); Michael Leung, Markham (CA); Beau Anthony Standish, Toronto (CA); Victor X. D. Yang, Toronto (CA)

(73) Assignee: 7D Surgical ULC., Toronto (CA)

( * ) Notice: Subject to any disclaimer, the term of this patent is extended or adjusted under 35 U.S.C. 154(b) by 246 days.

This patent is subject to a terminal disclaimer.

(21) Appl. No.: 17/020,052

(22) Filed: Sep. 14, 2020

(65) Prior Publication Data

US 2021/0065411 A1  Mar. 4, 2021

Related U.S. Application Data

(63) Continuation of application No. 16/510,078, filed on Jul. 12, 2019, now Pat. No. 10,789,739, which is a
(Continued)

(51) Int. Cl.
| | |
|---|---|
| *G06K 9/00* | (2022.01) |
| *G06T 11/00* | (2006.01) |
| *A61B 6/03* | (2006.01) |
| *A61B 5/055* | (2006.01) |
| *A61B 6/04* | (2006.01) |

(Continued)

(52) U.S. Cl.
CPC ............ *G06T 11/005* (2013.01); *A61B 5/055* (2013.01); *A61B 6/03* (2013.01); *A61B 6/032* (2013.01); *A61B 6/0492* (2013.01); *A61B 6/505* (2013.01); *A61B 6/5241* (2013.01); *G06T 3/0068* (2013.01); *G06T 7/33* (2017.01); *A61B 5/1077* (2013.01); *G06T 2207/10028* (2013.01);
(Continued)

(58) Field of Classification Search
CPC ...................................................... G06T 15/08
See application file for complete search history.

(56) References Cited

U.S. PATENT DOCUMENTS 10,013,777 B2 * 7/2018 Mariampillai ........ G06T 3/0068
10,403,009 B2 * 9/2019 Mariampillai ........... A61B 6/03
(Continued)

*Primary Examiner* — Hadi Akhavannik
(74) *Attorney, Agent, or Firm* — Hill & Schumacher

(57) ABSTRACT

The present disclosure relates to the generation of partial surface models from volumetric datasets for subsequent registration of such partial surface models to surface topology datasets. Specifically, given an object that is imaged using surface topology imaging and another volumetric modality, the volumetric dataset is processed in combination with an approach viewpoint to generate one or more partial surfaces of the object that will be visible to the surface topology imaging system. This procedure can eliminate internal structures from the surfaces generated from volumetric datasets, thus increases the similarity of the dataset between the two different modalities, enabling improved and quicker registration.

19 Claims, 16 Drawing Sheets

Related U.S. Application Data continuation of application No. 16/021,815, filed on Jun. 28, 2018, now Pat. No. 10,403,009, which is a continuation of application No. 15/034,128, filed as application No. PCT/CA2014/051120 on Nov. 25, 2014, now Pat. No. 10,013,777.

(60) Provisional application No. 61/908,385, filed on Nov. 25, 2013.

(51) Int. Cl.
*A61B 6/00* (2006.01)
*G06T 7/33* (2017.01)
*G06T 3/00* (2006.01)
*A61B 5/107* (2006.01)

(52) U.S. Cl.
CPC ............... *G06T 2207/10072* (2013.01); *G06T 2207/10081* (2013.01); *G06T 2207/30012* (2013.01)

(56) References Cited

U.S. PATENT DOCUMENTS

| | | | | |
|---|---|---|---|---|
| 10,789,739 | B2 * | 9/2020 | Mariampillai | A61B 6/505 |
| 2002/0065461 | A1 * | 5/2002 | Cosman | G06T 7/73 600/429 |
| 2007/0258645 | A1 * | 11/2007 | Gokturk | G06V 10/7557 382/190 |
| 2013/0060146 | A1 * | 3/2013 | Yang | G01B 11/25 600/476 |
| 2019/0333253 | A1 * | 10/2019 | Mariampillai | A61B 5/055 |

* cited by examiner

MERGED VIEWPOINTS

SYSTEM AND METHOD FOR GENERATING PARTIAL SURFACE FROM VOLUMETRIC DATA FOR REGISTRATION TO SURFACE TOPOLOGY IMAGE DATA

CROSS-REFERENCE TO RELATED APPLICATION

This application claims priority to U.S. Provisional Application No. 61/908,385, titled "SYSTEM AND METHOD FOR GENERATING PARTIAL SURFACE FROM VOLUMETRIC DATA FOR REGISTRATION TO SURFACE TOPOLOGY IMAGE DATA" and filed on Nov. 25, 2013, the entire contents of which is incorporated herein by reference.

BACKGROUND

The present disclosure relates to methods and systems for generating surface data from volumetric data. The present disclosure also relates to methods of registering volumetric data to surface data.

Surface to surface registration is important for many different applications such as rapid prototyping, spatial calibration procedures, and medical applications. Generally, in medical imaging surfaces are either derived from acquired volumetric datasets or directly from surface based imaging systems. In the first case, volumetric datasets belonging to patient anatomy, such as those acquired from whole-volume 3D imaging modalities like magnetic resonance imaging (MRI), computed tomography (CT), or ultrasound, are processed using algorithms such as marching cubes (Lorensen et al., 1987) to generate surfaces. With appropriate selection of intensity thresholds, the result is a surface representing a desired volume of interest. In the second case, surfaces of objects can be obtained by intrinsically surface based imaging such as optical range finding techniques like structured light imaging and laser range finding. With these techniques, the relative position of the surface topology imaging system to the object to be imaged determines which part of the surfaces will be visible to the imaging system and hence reconstructed.

Surfaces generated through marching cubes and related algorithms can be registered to other surface topology dataset using techniques such as iterative closest point, where the purpose of this registration is to align objects from different coordinate systems such that a spatial relationship may be established between the coordinate systems (e.g. from different imaging modalities). This has important clinical applications, such as in surgical navigation and other image-guided therapies.

SUMMARY

The present disclosure relates to the generation of partial surface models from volumetric datasets for subsequent registration of such partial surface models to surface topology datasets. Specifically, given an object that is imaged using surface topology imaging and another volumetric modality, the volumetric dataset is processed in combination with an approach viewpoint to generate one or more partial surfaces of the object that will be visible to the surface topology imaging system. This procedure can eliminate internal structures from the surfaces generated from volumetric datasets, thus increases the similarity of the dataset between the two different modalities, enabling improved and quicker registration.

Accordingly, in one aspect, there is provided a computer implemented method of performing image registration between volumetric image data associated with an object and surface topology image data associated with the object, wherein the surface topology image data is obtained by a surface topology imaging system, the method comprising:
 obtaining spatial information associated with the orientation of the surface topology imaging system relative to the object;
 processing the volumetric image data and the spatial information to generate one or more partial surfaces oriented toward the surface topology imaging system.

In another aspect, there is provided a system for measuring surface topology image data associated with an object and registering the surface topology image data to volumetric image data associated with the object, the system comprising:
 a surface topology imaging system; and
 processing and control hardware configured to:
  obtain spatial information associated with the orientation of the surface topology imaging system relative to the object;
  process volumetric image data and the spatial information to generate one or more partial surfaces oriented toward the surface topology imaging system.

A further understanding of the functional and advantageous aspects of the disclosure can be realized by reference to the following detailed description and drawings.

BRIEF DESCRIPTION OF DRAWINGS

Embodiments will now be described, by way of example only, with reference to the drawings, in which.

DETAILED DESCRIPTION

Figure 1A:
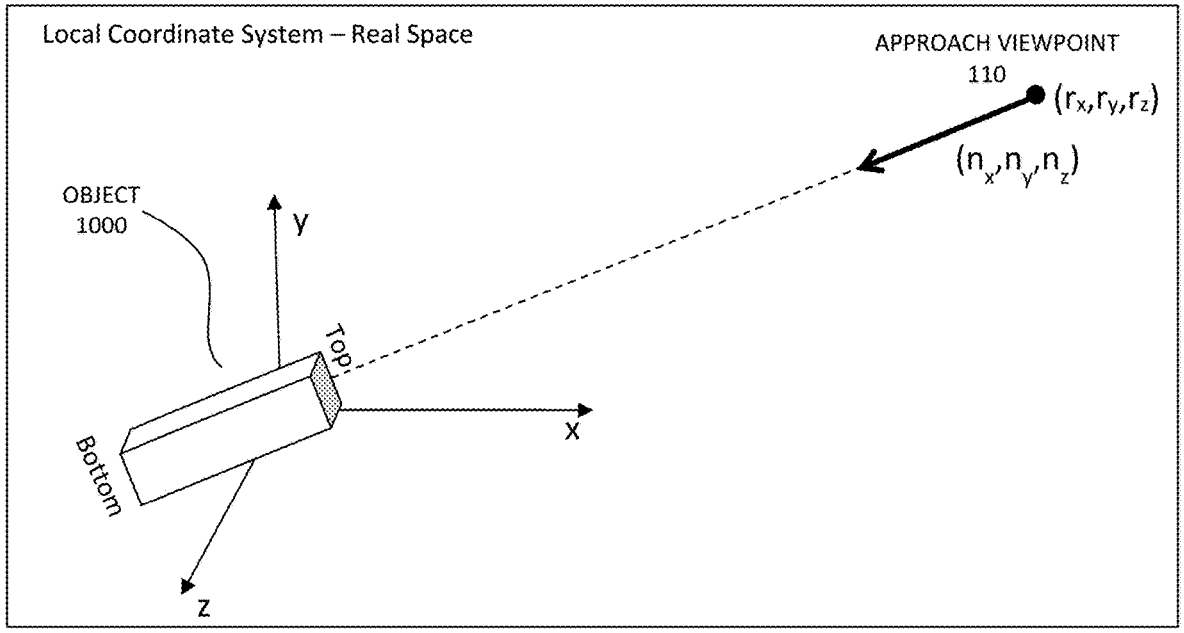
FIGS. 1A and 1B show a depiction of an object and approach viewpoint defined relative to local and virtual coordinate systems.

Various embodiments and aspects of the disclosure will be described with reference to details discussed below. The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosure.

It should be understood that the order of the steps of the methods disclosed herein is immaterial so long as the methods remain operable. Moreover, two or more steps may be conducted simultaneously or in a different order than recited herein unless otherwise specified.

As used herein, the terms "comprises" and "comprising" are to be construed as being inclusive and open ended, and not exclusive. Specifically, when used in the specification and claims, the terms "comprises" and "comprising" and variations thereof mean the specified features, steps or components are included. These terms are not to be interpreted to exclude the presence of other features, steps or components.

As used herein, the terms "about" and "approximately" are meant to cover variations that may exist in the upper and lower limits of the ranges of values, such as variations in properties, parameters. and dimensions. In one non-limiting example, the terms "about" and "approximately" mean plus or minus 10 percent or less.

Unless defined otherwise, all technical and scientific terms used herein are intended to have the same meaning as commonly understood to one of ordinary skill in the art. Unless otherwise indicated, such as through context, as used herein, the following terms are intended to have the following meanings:

As used herein, the phrase "partial surface" refers to a 3D representation (meshes, point clouds, contours, etc.) of a portion of a surface generated from volumetric data. A partial surface may be a portion of a surface associated with an object, where at least a portion of the partial of the surface is directed towards, visible from, not hidden from, and/or facing, a surface topology imaging system.

As outlined above, surfaces can be generated from 3D volumetric datasets using methods such as marching cubes. However, such surfaces, generated according to such methods, can contain both superficial and internal surface structures. In contrast, the surfaces captured in a dataset associated with a surface topology imaging system, such as a structured light based imaging system, are superficial in nature, and do not include internal surface structures. Furthermore, most surface topology imaging systems rely on line of sight so many regions of the object which may be superficial are still not captured. Such regions will henceforth be referred to as hidden surfaces.

For the purpose of image registration between the two modalities, internal structures and hidden surfaces are of limited use. In fact, the presence of these internal structures and hidden surfaces can cause the registration process to be slow (due to more data points present) and inaccurate (these surfaces are registered incorrectly to the actual surfaces of interest), in addition to requiring more memory for storage. Furthermore, it can be difficult to automatically remove these internal structures without the removal of pertinent information that are of interest, thus leading to the use of semi-automatic and/or user guided segmentation techniques.

The generation of these internal surfaces are particularly troublesome in medical imaging datasets. For example, in CT data, inhomogeneous hone structure (i.e. variations between cortical and cancellous bone), pathologies, and blurring can lead to improper reconstruction of conical surfaces and thus sub-optimal registration.

Various embodiments of the present disclosure utilize the orientation of the surface topology imaging system relative to the object being imaged to generate one or more partial surfaces from one or more volumetric datasets (such as, for example, CT, MRI or ultrasound volumetric datasets), which can then be registered with a surface topology dataset obtained by the surface topology imaging system. The use of partial surfaces, generated by the methods described herein, can improve the speed and accuracy of registering these partial surfaces to optical surface topology data, compared to methods that indiscriminately process the entire volumetric surface. Partial surfaces generated using the methods described herein contain regions that are directed towards (e.g. visible from, not hidden from, and/or facing) the optical surface topology system, and therefore would most likely be captured using the optical surface topology imaging system. This procedure therefore increases the similarity of the datasets between the volumetric and topology-based imaging modalities, leading to improved registration.

Figure 1B:
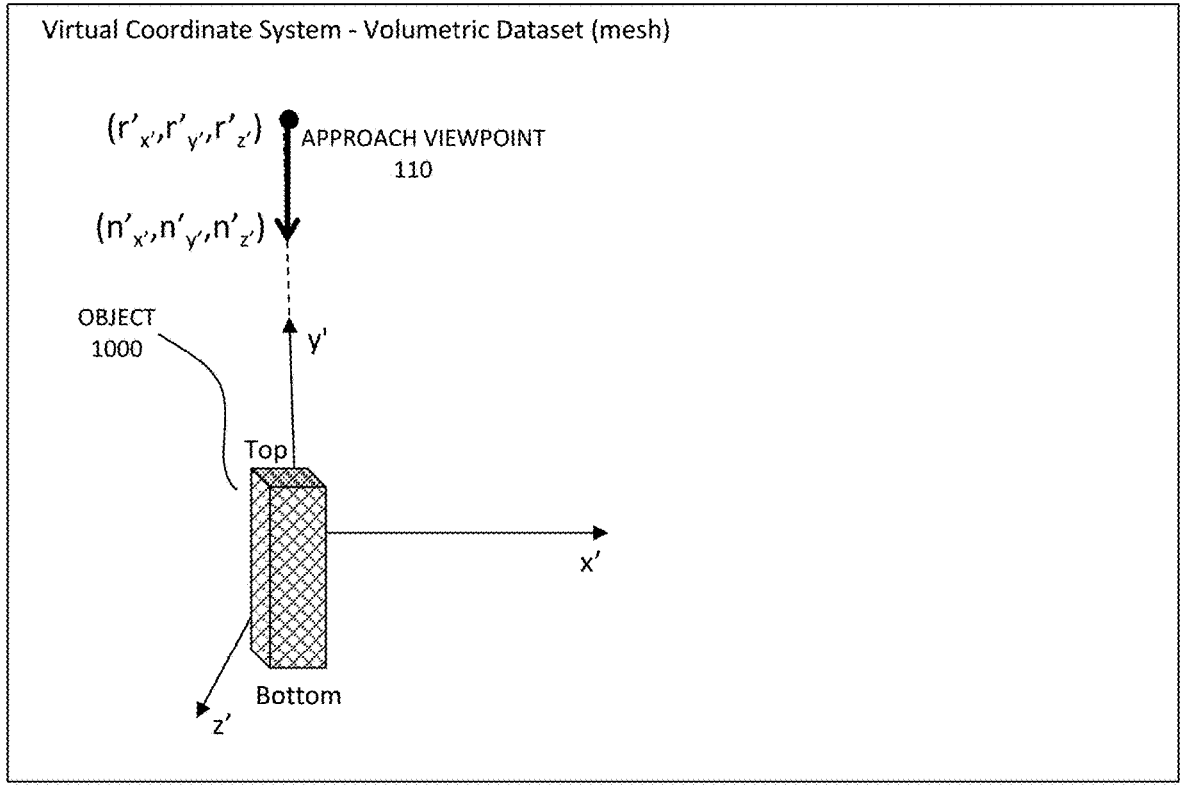

FIGS. 1A and 1B depict an object 1000 and an approach viewpoint 110 in (A) the local coordinate system defined by the x, y and z axes, and (B) the virtual coordinate system defined by the x', y' and z' axes. FIG. 1A shows the local coordinate system, which refers to the coordinate system that describes the position of an imaged object in a coordinate system that includes the surface topology imaging system. In surgical applications, this coordinate system could be relative to the patient, a stereotactic frame attached to the patient or with reference to the operating room. FIG. 1B shows the virtual coordinate system, which is the coordinate system in which the volumetric data (a 3D representation, stored in memory) associated with the imaged object is defined. For example, in medical imaging applications this could be the coordinate system defined in a DICOM image dataset. In another example involving an engineering application, this could be the coordinate system defined in a Computer Aided Design (CAD) file.

As described further below, partial surfaces may be generated from the volumetric data based on spatial information that is associated with the orientation of the surface topology imaging system relative to the object being imaged. This spatial information can be provided as any of a number of different measures. In some embodiments, the spatial information defines at least one "approach viewpoint" at a position 110 relative to the object of interest 1000, where the approach viewpoint is used to generate the partial surface based on the portions of the surface of the object that are visible from the approach viewpoint, based on the orientation of the object.

As noted above, there are many different measures that can be employed to define an approach viewpoint. For example, the approach viewpoint can be defined by providing the location (e.g. coordinates) of the approach viewpoint, and the location of a region of interest on the object, based on the estimated position and orientation of the object and the surface topology imaging system. The approach viewpoint may also be defined by a vector $(n_x, n_y, n_z)$ that points from a selected position $(r_x, r_y, r_z)$ to the region of interest of the object.

It will be understood that in most cases, only an approximate knowledge of the position and orientation of object 1000 within the both the virtual and local coordinate systems will be available. As described further below, an approximate transform relating these two coordinate systems and an approximate approach viewpoint are employed to generate a partial surface usable for registration. The degree of uncertainty in each of these parameters will be dependent on many factors, such as the specific application and the geometry of the object. Examples of these uncertainty ranges are given below with respect to particular applications and methods, and a discussion of cases in which these uncertainties become large are also provided in the present disclosure.

In the example embodiment shown in FIG. 1A, the local coordinate system is shown as being centered on the object 1000 (or on a region of interest associated with the object), where the object is provided in a given orientation relative to the axes of the local coordinate system. In such a case, the approach viewpoint can be defined by a position vector $(r_x, r_y, r_z)$ identifying a position relative to the origin. It will be understood, however, that the local coordinate system need not be centered on the object to be imaged (or centered on a region of interest of the object to be imaged), provided spatial information identifying the estimated position and orientation of the object is provided. In some embodiments, the approach viewpoint identifies the location (for example, a known (e.g. measured) location, an estimated location, an approximate location, or an expected location) of the surface topology imaging system, and the estimated or approximate direction of the line of sight between the surface topology imaging system and the object (the position and orientation of the object may not be known with high accuracy). In such embodiments, the approach viewpoint is employed to determine the partial surfaces that would be visible to the surface topology system based on its known, expected, or approximate location.

However, it will be understood that the approach viewpoint need not identify the location of the surface topology imaging system. For example, the approach viewpoint may identify a location along an axis defining the estimated or approximate line of sight between the surface topology imaging system and the object (or a region of interest on the object, such as, for example, the center of the object, a particular location on the object, or a particular feature on the object).

In other embodiments, the approach viewpoint need not lie on the estimated or approximate line of sight axis. Instead, an approach viewpoint can be defined such that at least a portion of the surface visible from the approach viewpoint would also be visible to (e.g. measurable by) the surface topology imaging system, where the portion of the object surface that represents the overlap between the surface visible from the approach viewpoint, and the surface visible from the surface topology imaging system, would be sufficient to perform image registration.

In some embodiments, an approach viewpoint may be defined relative to a known geometrical property of the object, based on an expected or estimated position and orientation of the object relative to the surface topology imaging system. For example, in one example implementation involving a surgical procedure, it may be known in advance that the patient will be positioned (at least approximately) in a particular orientation, such that an anatomical surface or feature will be directed toward, or visible from, the surface topology imaging system. In such a case, an approach viewpoint may be defined relative to the known patient orientation (or the known orientation of the anatomical surface or feature).

For example, if it is known that a spinal surgical procedure is to be performed on a patient lying in the prone position, and that surface topology measurements are to be performed in an overhead configuration (e.g. directly overhead, or overhead at an offset angle), then an approach viewpoint may be estimated or approximated at a point lying above the surgical region of interest. In one example implementation pertaining to such a surgical procedure, an approach viewpoint may be defined above the surgical region, along a direction that is approximately normal to the coronal plane. In a more general implementation, an approach viewpoint could be defined at a point lying above the surgical region of interest, and within an angular deviation relative to a direction normal to the coronal plane, where the angular range is sufficiently narrow to permit sufficient visibility of the region of interest (e.g. such that the local height variations of the object within the region of interest do not preclude the generation of a partial surface through excessive shadowing within the region of interest).

As noted above, the approach viewpoint is defined within the local coordinate system. In order to proceed with generation of one or more partial surfaces based on the volumetric data (defined in the virtual coordinate system), the approach viewpoint is transformed into the virtual coordinate system by identifying a suitable transformation between the local coordinate system and the virtual coordinate system.

This determination of the orientation of the approach viewpoint within the virtual coordinate system may be performed (e.g. estimated), for example, based on knowledge (e.g. an estimate) of the orientation of the object to be imaged in both the local coordinate system and in the virtual coordinate system, by employing orientation information that describes the approximate orientation of the object in the volumetric dataset, such as information provided in a DICOM header file. This orientation information may be employed to generate a transformation $T_{LV}$ based on the knowledge of the orientation of the object in the local coordinate system. This transformation may then be employed to transform the approach viewpoint into the virtual reference frame, as shown in FIG. 1B, which illustrates an example in which the top and bottom of the object are in a known orientation (along the y' axis) in the virtual coordinate system and the approach viewpoint is depicted as being above the "top" of the object. Although FIG. 1B shows the approach viewpoint being transformed to lie exactly along the axis of the object (as in the local coordinate system shown in FIG. 1A), it will be understood that this transformation is an approximate transformation, and that in many cases the alignment of the transformed approach viewpoint relative to the object in the virtual coordinate system will only be an approximate alignment.

In medical imaging applications similar information is stored in the header of the DICOM file. The header specifies the orientation in which the patient was scanned, for example, prone or supine and head or feet first. This information is used to define unambiguously the head-foot direction, anterior-posterior direction and the left-right direction in the virtual coordinate system. This same anatomical coordinate system is used to plan medical interventions and thus readily understood/specified by the practitioner.

Figure 2:
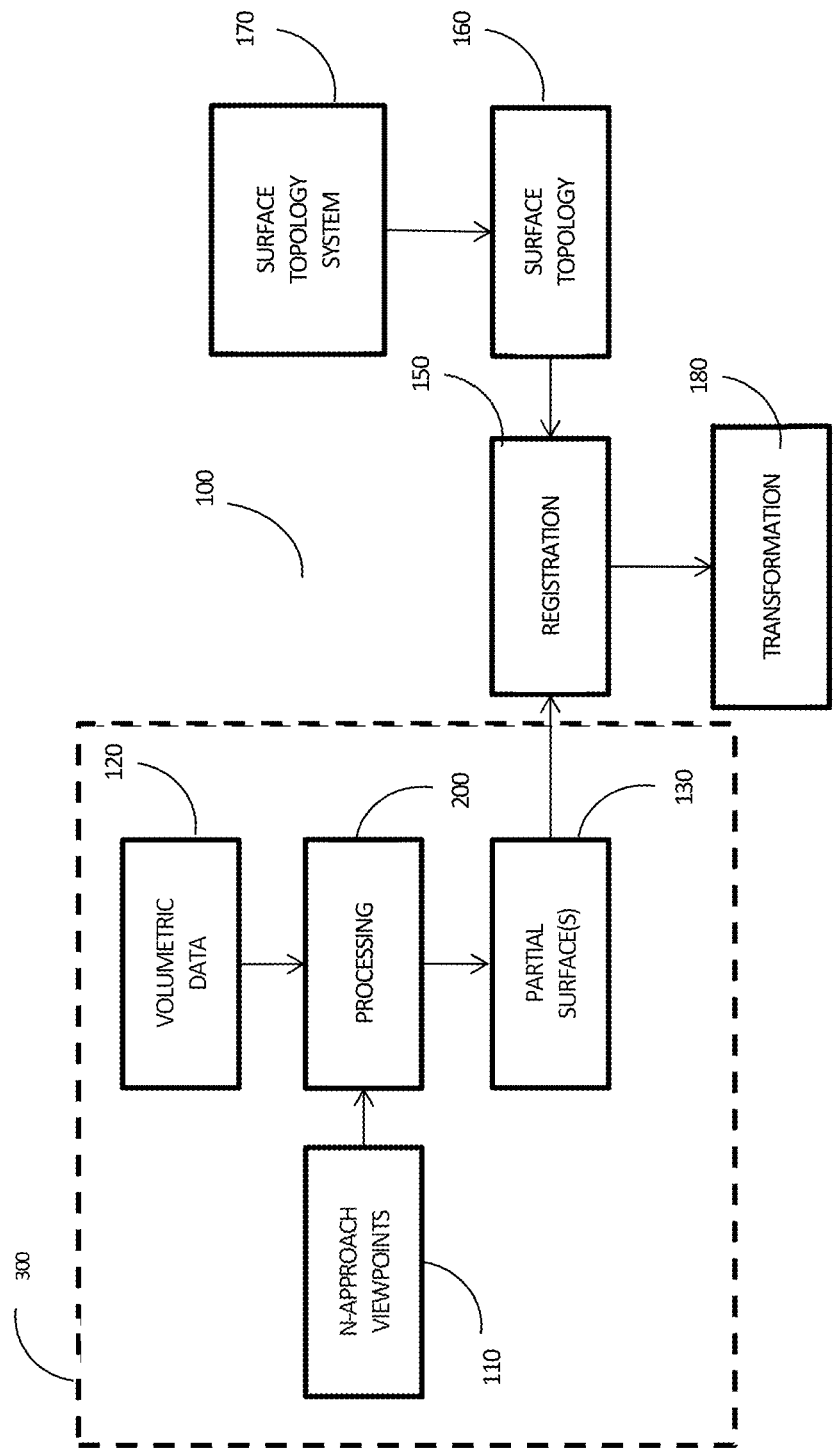
FIG. 2 is a flow chart illustrating an example implementation of a method of generating partial surface data from volumetric image data, and registering the partial surface data to surface topology data.

FIG. 2 provides a flow chart illustrating an example implementation of a method of generating partial surface data from volumetric image data, and registering the partial surface data to surface topology data. The generation of partial surface data based on volumetric image data is illustrated by the method steps illustrated within dashed box 300. As shown at steps 110 and 120, one or more approach viewpoints and volumetric datasets are provided as input(s) and are processed at step 200 to generate one or more partial surfaces, as shown at step 140. As described further below, the volumetric data is processed at step 200 to generate at least one partial surface for each approach viewpoint. The volumetric data provided at step 120 can be any one of a number of forms including, for example, point clouds, meshes and intensity images stacks, non-limiting examples of which are: DICOM, TIFF, JPEG, STL, PLY, PNG, OBJ, and VTP.

As shown at step 110, one or more approach viewpoints are provided as an input to the partial surface processing step 200. This can be achieved, for example, prospectively, retrospectively or in real-time. For example, in one example implementation using a retrospective method, the surface topology data 160 can be acquired first, before defining or providing the one or more approach viewpoints (at 110), thus enabling the user to specify the one or more approach viewpoints while visualizing surface topology dataset 160. Alternatively, in another example implementation using a prospective method, one or more approach viewpoints can be specified. For example, the one or more approach viewpoints may be selected based on pre-selected, expected, and/or preferred orientations of the surface topology system relative to the object to be imaged. In other embodiments a regular grid of approach viewpoints could be specified, for example, a regular grid (in terms of solid angle) on the surface of sphere surrounding the object to be imaged. In some applications, it may be useful to create multiple partial surfaces for different intersection criteria, such as intensity value or other parameter. For example, in one example implementation, it could be useful to employ this approach for cranial procedures, where surfaces are generated for the skin, bone, brain and perhaps a tumor surface, in order to guide various aspects of a surgical procedure.

In a real-time or approximately real-time example implementation, position information that is provided in real time or approximately in real time by position sensors can be processed to determine the location and orientation of the surface topology system. The generation of partial surfaces can then proceed in real time or approximately in real time.

For example, in some embodiments, a plurality of approach viewpoints may be specified that cover a range of possible positions and orientations that the surface topology system or apparatus may have relative to the object being imaged during the imaging process. A partial surface may be generated for each approach viewpoint, thereby providing a set of partial surfaces and associated approach viewpoints. In order to perform image registration for a given orientation of the surface topology imaging system, the actual approach viewpoint may be compared with the set of approach viewpoints, in order to determine the approach viewpoint that best matches the actual approach viewpoint. Image registration may then be performed based on the partial surface corresponding to the approach viewpoint providing the best match.

In one example implementation, the approach viewpoint with the best match may be selected manually (for example, from a list of potential approach viewpoints). In another example implementation, the approach viewpoint with the best match may be selected automatically. For example, the appropriate approach viewpoint could be selected by the observation or detection of fiducial markers attached to, or present on, the object (and optionally the surface topology imaging system). This fiducial could be detected by any number of sensors including acoustic, optical and electromagnetic.

Also, in some practical situations where the surface topology system is positioned manually, it is possible that the actual approach viewpoint is only known approximately. In such a case, generating a partial surface from an approximate approach viewpoint may yield a partial surface that does not include all of the relevant portions of the surface that are imaged by the surface topology system. Accordingly, by specifying a plurality of approach viewpoints that sample, approximate, and/or span the ranges of positions and orientations that are achieved by manual positioning, a set of partial surfaces can be generated, and a composite surface can be generated based on the union of the set of surfaces. The composite surface may have an increased overlap with the surfaces generated by the surface topology imaging system, which can aid the registration process. In one example implementation, the individual partial surfaces from the set of partial surfaces may be combined by a simple union (addition) of the multiple partial surfaces in the case of point clouds. While this may lead uneven point cloud density in overlapping regions, this can be processed by removing/merging points within a certain specified spatial tolerance of one another. This tolerance can be an absolute distance from the mean or median of a fixed number of points, or alternatively based on the standard deviation. In some implementations, the search may be accomplished using a spatial point locator to quickly search for points in 3D. Non-limiting examples of such locators are rectangular buckets, kd-trees and octrees.

Furthermore, in practical situations, the approach viewpoint(s) should be selected so there is sufficient spatial overlap between the set of partial surfaces and the surface generated by the surface topology imaging system. This can aid in the registration process. The choice of approach viewpoint is dependent on the field of view of the surface topology imaging system, and the geometry of the anatomy, which can block certain regions of interest due to the line of sight requirement of the surface topology imaging system, as well as the approach viewpoint trajectories used to generate the partial surfaces. Example choices of the approach viewpoints used for posterior approach spine surgery is described in later sections.

Those skilled in the art will realize that registration of two surfaces is dependent on a number of factors that are specific to the uniqueness of the geometry of the object of interest and application. One of such factors is the minimum number of overlapping features that are present in both surfaces. Examples that illustrate this point are listed below with respect to posterior approach spine surgery where the object of interest is the vertebrae. In typical scenarios, geometrical features relating to anatomical sites that are exposed on the vertebrae include the spinous process, the articular process (there are 2), and the lamina (there are 2). Out of these five features, a subset of them must be present in both the generated partial surface and surface generated from the surface topology imaging system for registration to be successful.

Theoretically, only one such geometrical feature is required for the registration of two surfaces. However, ambiguities brought on by symmetries in the object's geometry and sources of noise that include those from the imaging system, and in the case of open spine surgery where the target of interest is the vertebrae, blood and tissue that can obscure the bone, make this impractical.

With respect to the application above, in one scenario, if an initial alignment is present so that the two surfaces are approximately aligned, then registration requires a minimum of two such overlapping geometrical features in both the generated partial surface and surface generated from the surface topology imaging system.

This approximate alignment can be defined by the user, for example, by selecting 3 approximately co-localized points in both surfaces. Approximately aligned, in this context, means that the features on one surface are positioned so that they are no further away from the corresponding features in the other surface by half the distance between the 2 geometrical features.

With respect to the application above, in another scenario, if no initial alignment is available, then registration requires a minimum of three such overlapping geometrical features in both the generated partial surface and surface generated from the surface topology imaging system.

These examples relate to practical scenarios for posterior approach spine surgery. The number of required features can decrease if the geometry is sufficiently unique, or can increase otherwise. For example, in neurosurgical procedures, it may be possible to use a single anatomical feature or a portion of a single anatomical feature on the head (ear, chin, nose) to successfully perform surface registration. This is in part due to the lack of anatomical noise compared the case of posterior approach spine surgery.

In some embodiments, the one or more approach viewpoints can be defined manually using a user interface or, for example, via one or more data files. In some example implementations, the one or more approach viewpoints can be provided by a user, where, for example, the input could be a keyboard, touchscreen, stylus or microphone (for example, using voice commands). For example, in the application of cranial neurosurgery, the generation of partial surfaces of the head (e.g. soft tissue or bone) could be utilized for registration as part of a structured light based surgical navigation system as described, for example, in PCT Application No. PCT/CA2011/050257, titled "SYSTEM AND METHODS FOR INTRAOPERATIVE GUIDANCE FEEDBACK", which is herein incorporated by reference in its entirety. In this application, a surgeon may choose to take either a posterior or anterior approach during a particular surgical intervention. This could be specified during the startup of the structured light surgical navigation system software through a user interface. The surgeon would then specify the anterior or posterior approach by selecting the respective option. The software would subsequently use this information with a user loaded CT/MRI DICOM image dataset and associated header information of the patient's head to subsequently generate the partial surface from the anterior or posterior approach viewpoint.

In more arbitrary situations, where a pure posterior or anterior approach may not be used, the surgeon could select the surface topology imaging system viewpoint for the intervention with respect to a 3D model (i.e. isosurface rendering) of the patients head/skull by rotating the camera viewpoint about the model. The camera viewpoint could then used as an estimate of the approach viewpoint. In either the pure anterior/posterior approach, or in the case of a more arbitrary approach, the surgeon would be able to adjust the position and orientation of the structured light surgical navigation system to match the specified approach viewpoint as closely as possible before proceeding with the procedure.

Figure 3:
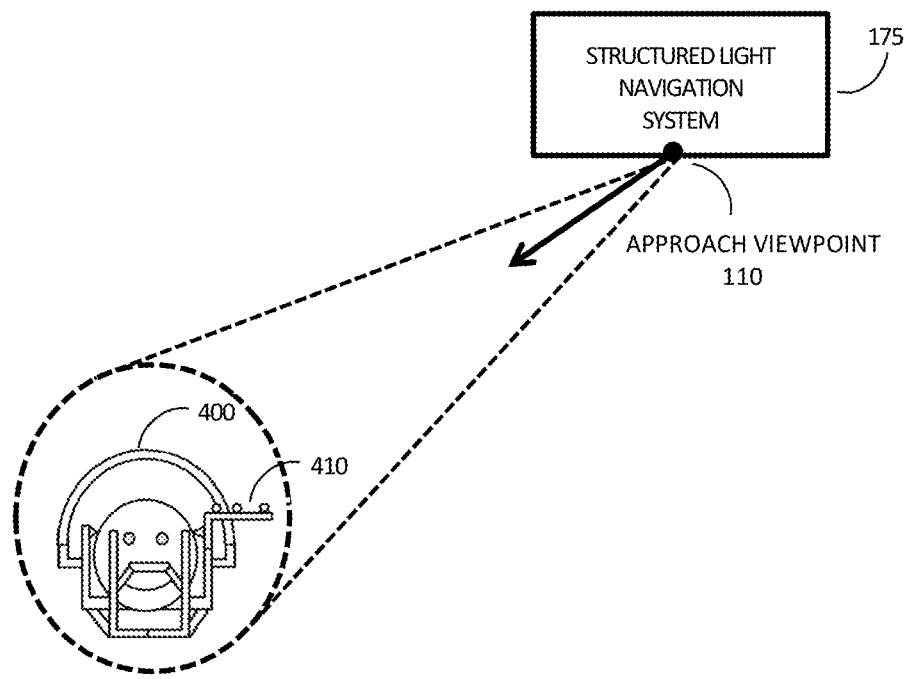
FIG. 3 is an illustration showing a patient undergoing stereotactic neurosurgery using a structured light surgical navigation system.

In other example implementations, the one or more approach viewpoints may be automatically determined or obtained, for example, using position/orientation information sensors, such as radio frequency, optical, electromagnetic, or mechanical sensors. For example, FIG. 3 shows a schematic of a patient undergoing stereotactic neurosurgery using a structured light surgical navigation system 175 as discussed above. A stereotactic frame 400 is attached to the patient's skull in a standard predefined orientation (i.e. the frame is attached to an individual's head in a particular orientation). A reference marker 410, which is optically tracked by the surgical navigation system and is fixed (incorporated so that its orientation and position relative to the stereotactic frame is known a priori) to the stereotactic frame. Since the stereotactic frame and thus the reference marker have a known orientation relative to the patient's skull the structured light surgical navigation system 175 is able to determine the approach viewpoint 110 by tracking the reference marker positions orientation. This position and orientation can then be used in conjunction with DICOM image dataset and associated header information to generate the relevant partial surface(s).

Referring again to FIG. 2, according to one embodiment, the one or more partial surfaces may be registered, as shown at step 150, to surface topology data (provided at as shown at 160) to generate the registration transformation at step 180. Registration may be based, for example, on rigid body methods, deformable methods, or a combination thereof.

Non-limiting examples of rigid body surface registration techniques include landmark registration, singular value decomposition (SVD) and iterative closest point (ICP) registration and its many variants. Examples of suitable methods of surface registration are described in Chen and Medioni (Y. Chen and G. Medioni, "Object Modeling by Registration of Multiple Range Images", Proc. IEEE Conf. on Robotics and Automation, 1991) and Besl and McKay (P. Besl and N. McKay, "A Method for Registration of 3D Shapes", IEEE Trans. Pattern Analysis and Machine Intelligence 14 (1992), 239).

It should emphasized that some registration methods may require user input in order to proceed. For example, landmark registration, which is typically used as a rough registration precursor to ICP, requires matched points pairs to be picked on both the surfaces. These pairs are usually specified through a user interface and input device. Typically, 3 pairs of user defined points are employed for the transform to be well defined, however this can be relaxed by using data associated with a single picked point (normals, curvatures) and/or a priori information (a known axis or direction inputted by the user or detected by the system) to automatically generate the three or more points from the single user defined point. As alluded to above, multi-step registration processes are very common/useful since ICP based methods have tendency to become trapped in local minima, thus a crude estimate (i.e. registration that is obtained through the use of a landmark transform or SVD) of the registration transform is usually necessary to use these methods successfully.

In other embodiments, deformable registration can also be used to register the surface topology 160 to partial surfaces 140. Non-limiting examples of deformable registration methods include kernel splines methods (such as thin plates, thin plates $R^2$ log R, elastic body, elastic body reciprocal, and volume) and demon registration methods and its variants.

The output transformation, obtained at step 180 after having performed registration, can be, in the case of rigid body registration, a transformation matrix including translation and rotation information. For example, translation identities can be present on an x, y, z coordinate system with rotation represented by roll, pitch, and yaw identities. It is recognized that transformation matrices can be based on alternative coordinate systems, or represented by different mathematical descriptions like quaternions In the case of deformable registration, the output transformation may be, for example, a vector field or a mapping function which transforms points from one coordinate system to the other.

Figure 4:
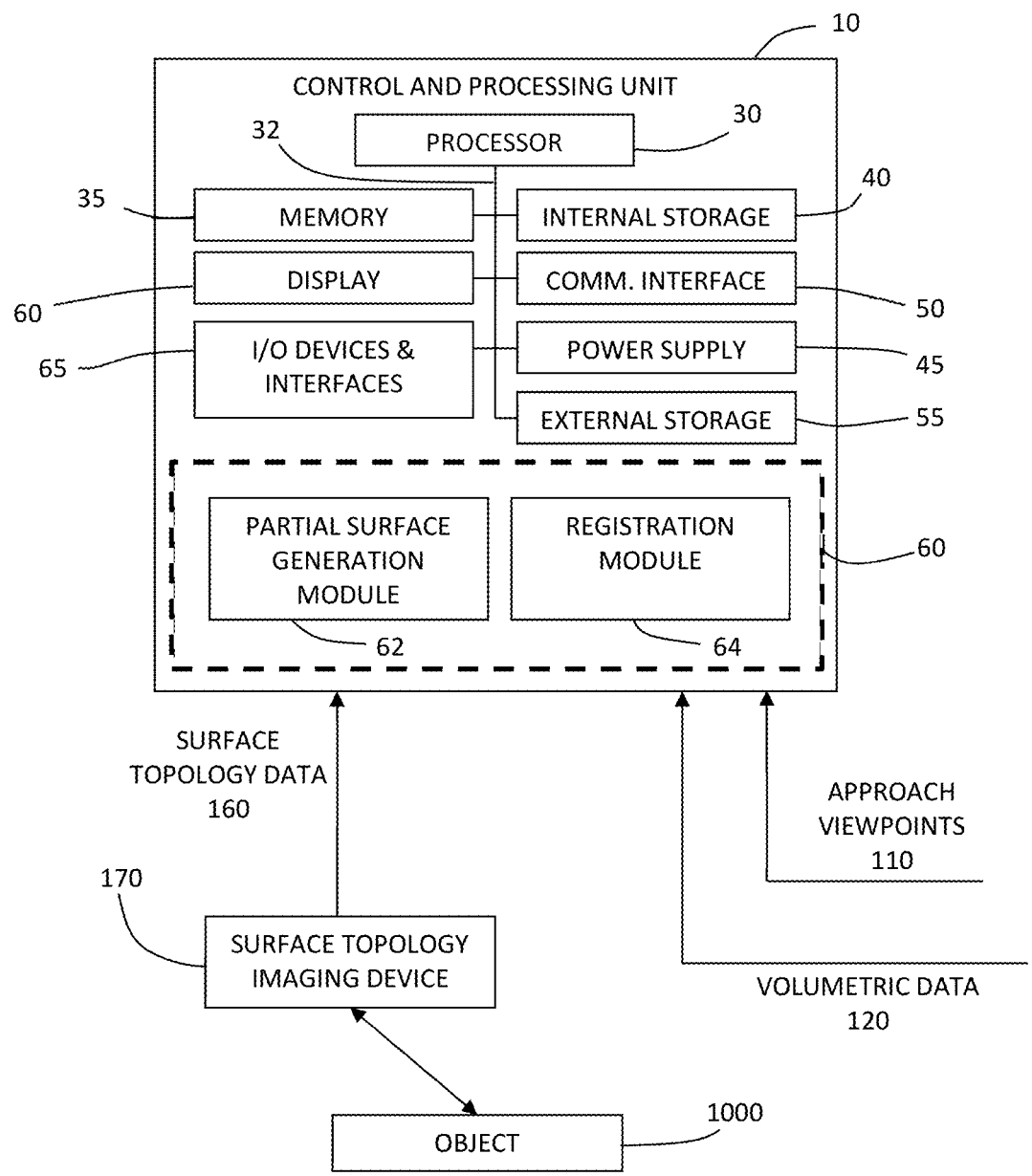
FIG. 4 is a block diagram illustrating an example implementation of a system for performing partial surface generation.

FIG. 4 provides a block diagram illustrating an example implementation of a system for performing partial surface generation based on one or more input approach viewpoints, and optionally for performing subsequent registration to surface topology image data. Volumetric data 120 and one or more approach viewpoints 110 are provided to control and processing unit 10, which processes these inputs to generate a partial surface, according to the embodiments disclosed herein. Surface topology imaging device 170 scans object 1000, and surface topology data 160 is provided to control and processing unit 10, which is processed with the partial surface to obtain a suitable transformation for surface registration. Data such as volumetric data 70 and surface topology data 160 may be stored, for example, in memory 35, internal storage 40, and/or external storage 55.

Surface topology system 170 may be any suitable system for detecting, measuring, imaging, or otherwise determining the surface topology of one or more objects using optical radiation or sound waves (e.g. ultrasound). Non-limiting examples of suitable optical devices include laser range finders, photogrammetry systems, and structured light imaging systems. which project surface topology detection light onto a region of interest, and detect surface topology light that is scattered or reflected from the region of interest. The detected optical signals can be used to generate surface topology datasets consisting of point clouds or meshes. Other examples using sound waves for determining surface topology can include ultrasonography.

FIG. 4 provides an example implementation of control and processing unit 10, which includes one or more processors 30 (for example, a CPU/microprocessor or a graphical processing unit, or a combination of a central processing unit or graphical processing unit), bus 32, memory 35, which may include random access memory (RAM) and/or read only memory (ROM), one or more internal storage devices 40 (e.g. a hard disk drive, compact disk drive or internal flash memory), a power supply 45, one more communications interfaces 50, external storage 55, a display 60 and various input/output devices and/or interfaces 55 (e.g., a receiver, a transmitter, a speaker, a display, an imaging sensor, such as those used in a digital still camera or digital video camera, a clock, an output port, a user input device, such as a keyboard, a keypad, a mouse, a position tracked stylus, a position tracked probe, a foot switch, and/or a microphone for capturing speech commands).

Control and processing unit 10 may be programmed with programs, subroutines, applications or modules 60, which include executable instructions, which when executed by the processor, causes the system to perform one or more methods described in the disclosure. Such instructions may be stored, for example, in memory 35 and/or internal storage 40. In particular, in the example embodiment shown, partial surface generation module 62 includes executable instructions for generating a partial surface from volumetric data based on one or more approach viewpoints, in accordance with one or more of the methods embodiments disclosed herein. For example, partial surface generation module 62 may include executable instructions for generating a partial surface based on a ray casting method as described below. Registration module 64 includes executable instructions for registering a computed partial surface w the surface topology data 80.

Although only one of each component is illustrated in FIG. 4, any number of each component can be included in the control and processing unit 10. For example, a computer typically contains a number of different data storage media. Furthermore, although bus 32 is depicted as a single connection between all of the components, it will be appreciated that the bus 32 may represent one or more circuits, devices or communication channels which link two or more of the components. For example, in personal computers, bus 32 often includes or is a motherboard. Control and processing unit 10 may include many more or less components than those shown.

In one embodiment, control and processing unit 10 may be, or include, a general purpose computer or any other hardware equivalents. Control and processing unit 10 may also be implemented as one or more physical devices that are coupled to processor 130 through one of more communications channels or interfaces. For example, control and processing unit 10 can be implemented using application specific integrated circuits (ASICs). Alternatively, control and processing unit 10 can be implemented as a combination of hardware and software, where the software is loaded into the processor from the memory or over a network connection. For example, connections between various components and/or modules in FIG. 2, which enable communications of signals or data between various systems, may be a direct connection such as a bus or physical cable (e.g. for delivering an electrical or optical signal), such a LAN or WAN connections, or may be a wireless connection, for example, as an optical transmission modality, or wireless transmission modality such as Wifi, NFC or Zigbee®.

While some embodiments have been described in the context of fully functioning computers and computer systems, those skilled in the art will appreciate that various embodiments are capable of being distributed as a program product in a variety of forms and arc capable of being applied regardless of the particular type of machine or computer readable media used to actually effect the distribution.

A computer readable medium can be used to store software and data which when executed by a data processing system causes the system to perform various methods. The executable software and data can be stored in various places including for example ROM, volatile RAM, non-volatile memory and/or cache. Portions of this software and/or data can be stored in any one of these storage devices. In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

Examples of computer-readable media include but are not limited to recordable and non-recordable type media such as volatile and non-volatile memory devices, read only memory (ROM), random access memory (RAM), flash memory devices, floppy and other removable disks, magnetic disk storage media, optical storage media (e.g., compact discs (CDs), digital versatile disks (DVDs), etc.), among others. The instructions can be embodied in digital and analog communication links for electrical, optical, acoustical or other forms of propagated signals, such as carrier waves, infrared signals, digital signals, and the like. As used herein, the phrases "computer readable material" and "computer readable storage medium" refers to all computer-readable media, except for a transitory propagating signal per se.

Some aspects of the present disclosure can be embodied, at least in part, in software. That is, the techniques can be carried out in a computer system or other data processing system in response to its processor, such as a microprocessor, executing sequences of instructions contained in a memory, such as ROM, volatile RAM, non-volatile memory, cache, magnetic and optical disks, or a remote storage device. Further, the instructions can be downloaded into a computing device over a data network in a form of compiled and linked version. Alternatively, the logic to perform the processes as discussed above could be implemented in additional computer and/or machine readable media, such as discrete hardware components as large-scale integrated circuits (LSI's), application-specific integrated circuits (ASIC's), or firmware such as electrically erasable programmable read-only memory (EEPROM's) and field-programmable gate arrays (FPGAs).

Figure 5:
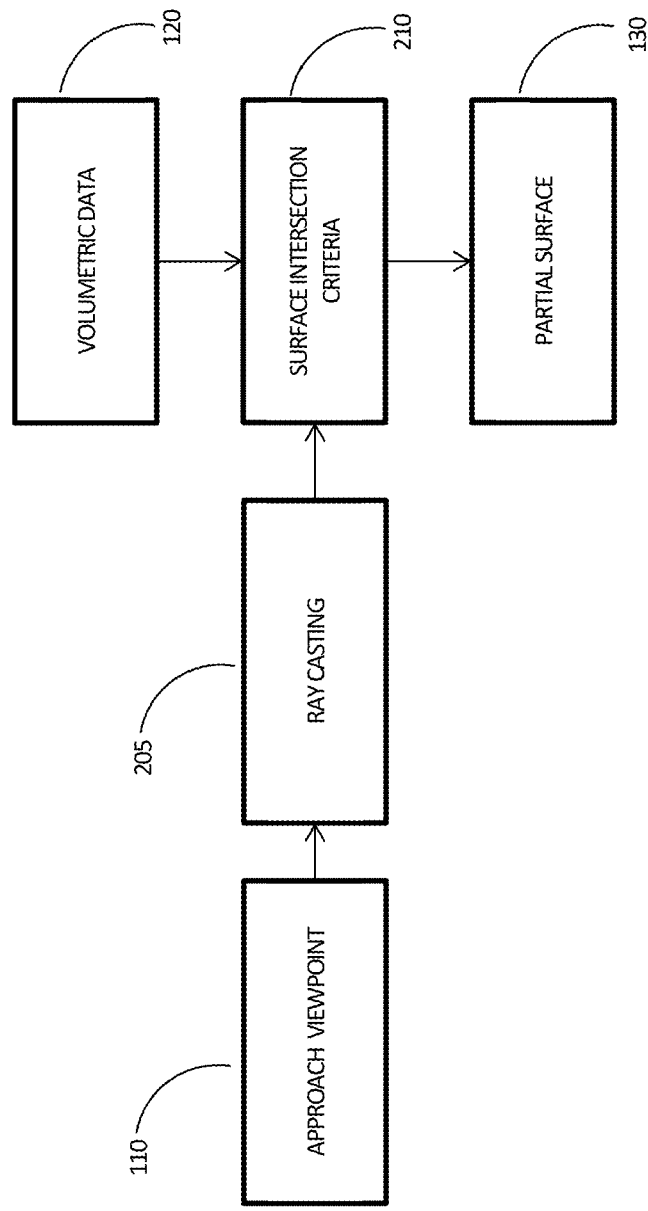
FIG. 5 is a flow chart showing an example method of generating a partial surface from volumetric data based on a single approach viewpoint.

FIG. 5 provides a more detailed flow chart of an example method of generating a partial surface from volumetric data based on a single approach viewpoint. This approach viewpoint 110 is used to generate a set of rays 205 that are cast onto the volumetric data 120. The approach viewpoint may be chosen according to different criteria or physical and space restrictions associated with where the surface topology imaging system 170 can be placed relative to object 1000. Surface topology imaging system 170 acquires a surface topology dataset 160 from the perspective of approach viewpoint 110, which is then processed to create a topology dataset 160 of the object's surface.

Figure 6A:
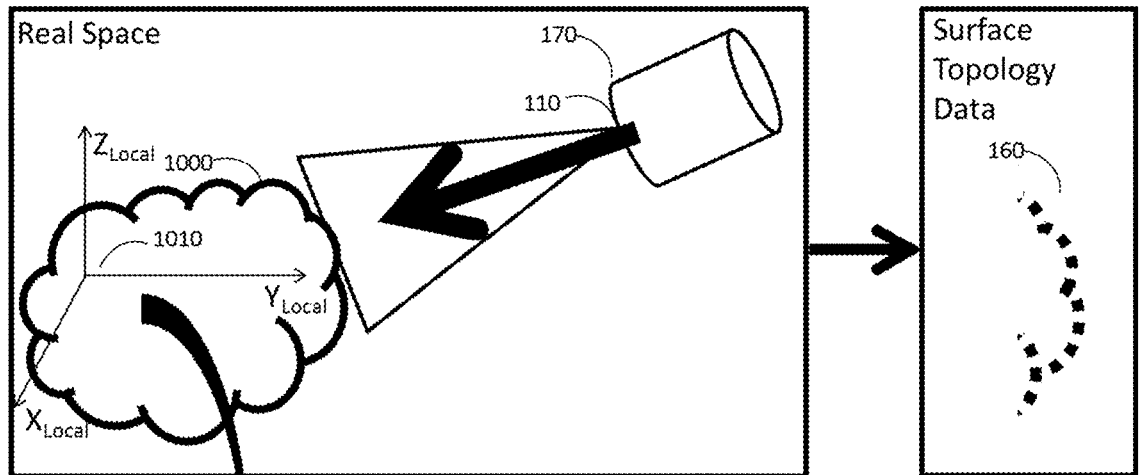
FIGS. 6A and 6B illustrate an example method of ray casting.

This method of ray casting is illustrated with reference to FIGS. 6A and 6B. FIG. 6A depicts a scenario in which an object 1000 in real space (i.e. the physical world) is imaged using a surface topology imaging system 170 from an approach viewpoint 110.

As noted above, the approach viewpoint is initially defined in the local coordinate system 1010 relative to the object being imaged. However, in order to proceed with the generation of a partial surface in the virtual reference frame in which the volumetric image data is defined, the orientation and position of the approach viewpoint 110 in the virtual reference frame is determined. This determination of the orientation and position of the approach viewpoint within the virtual reference frame may be performed, for example, based on knowledge of the orientation of the object to be imaged in both the real space reference frame 1010 and in the virtual reference frame 1020 by employing orientation information that describes the orientation of the object in the volumetric dataset, such as information provided in a DICOM header file. This orientation information may be employed to generate a transformation $T_{LV}$ based on the knowledge of the estimated or approximate orientation of the object in the local coordinate system. This transformation may then be employed to transform the approach viewpoint into the virtual reference frame, as shown in FIG. 6B.

Figure 6B:
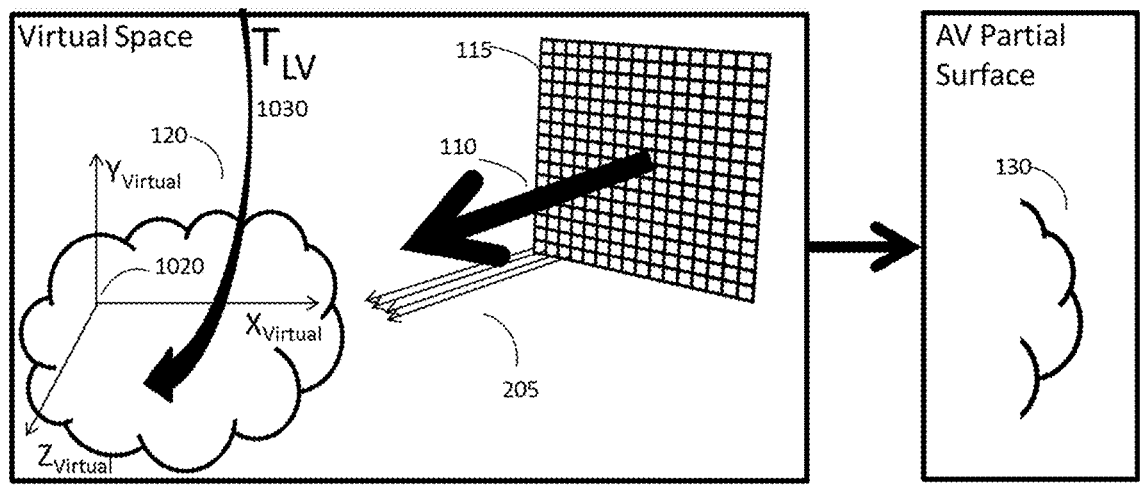

FIG. 6B depicts how ray casting 205 can be used to generate the corresponding partial surface 130 based on an orthographic projection (parallel ray projection) of volumetric dataset 120 of the object 1000 onto a plane 115 defined by viewpoint 110 and a specified spatial extent in virtual space. More generally, perspective transforms could be substituted for orthographic projection.

As noted above, the approach viewpoint 110 must first be transformed using $T_{LV}$ in order to move the approach viewpoint from the local coordinate system in real space into the virtual coordinate system.

Referring again to FIG. 5, a surface intersection criteria 210 is specified such that each ray is cast into the volumetric dataset 120 until it passes a point that meets a specified surface intersection criteria 210. The point and associated data (e.g. normals, textures, curvatures etc.) are then saved to generate partial surface 130.

Depending on the type of volumetric data provided as input to the method depicted in flow chart 300, various surface intersection criteria 210 between incident rays and volumetric data can be utilized. For example, threshold intensity values, or gradients of intensity values may be used to specify a surface intersection criteria such as intensity value greater than a given threshold value, or intensity gradient-based processing. In other embodiments, the surface intersection may be a combination of several different criteria such as an intensity value greater than a given threshold value, in combination with gradient-based processing. For example, in the case of intersection criteria for dense cortical bone in CT image data an intensity threshold value would typically be 1000 Hounsfield units. However, it will be understood that these number can vary widely depending on the age and health of the patient and any pathologies that may be present. An example method in which intensity gradients are used to specify air-skin and skin-fat interfaces in MRI of the breast is provided in Nie K., Chen J. H., Chan S., Chau M. K., Yu H. J., Bahri S., Tseng T., Nalcioglu O., and Su M. Y., "Development of a quantitative method for analysis of breast density based on three-dimensional breast MRI," Med. Phys. 35, 5253-5262 (2008) .10.1118/1.3002306.

It should also be emphasized that multiple intersection criteria may be specified to generate multiple partial surfaces pertaining to different structures within the volumetric data. This would be particularly useful in scenarios where different portions of the patient or object being imaged are exposed during a particular process or procedure. For example, in a neurosurgical application, one may define multiple surface intersection criteria which generate partial surfaces associated with the skin, cortical bone and/or brain surface. As the surgeon traverses these layers during a procedure, a partial surface corresponding to the exposed surface would be utilized.

In some embodiments, a first hit protocol is used to generate partial surfaces 130. A first hit protocol can be defined, for example, using intensity values or gradients of intensity. For example, each ray may be cast onto the volumetric data set and the first point intersected along the ray with a value greater than a threshold is saved to the partial surface 130. All subsequent points that intersect the ray which passes the intersection criteria are ignored.

In cases where noise may be an issue, a more stringent criterion is beneficial, which requires M consecutive points to satisfy the intersection criteria 210 before it may be added to the final partial surface. Specifically, the ray is traversed and when M points are found sequentially to meet the surface intersection criteria 210, one of the points, which may be specified as part of the surface intersection criteria 210 (e.g. the first point the ray intersects with, or the point equidistant from the first and last point), is saved to partial surface 215.

In some embodiments, this concept can be further extended by processing data within the local 2D and/or 3D neighborhood of each ray to define the intersection criteria. That is, the surface intersection criteria 210 is specified in such a way that, as each new point is examined to determine whether the surface intersection criteria 210 has been met, the neighboring points are also examined. A non-limiting example of such a surface intersection criteria 210 is a mean intensity value over a local neighborhood of points within a radius R (of the current point) greater than a threshold value X.

Figure 7:
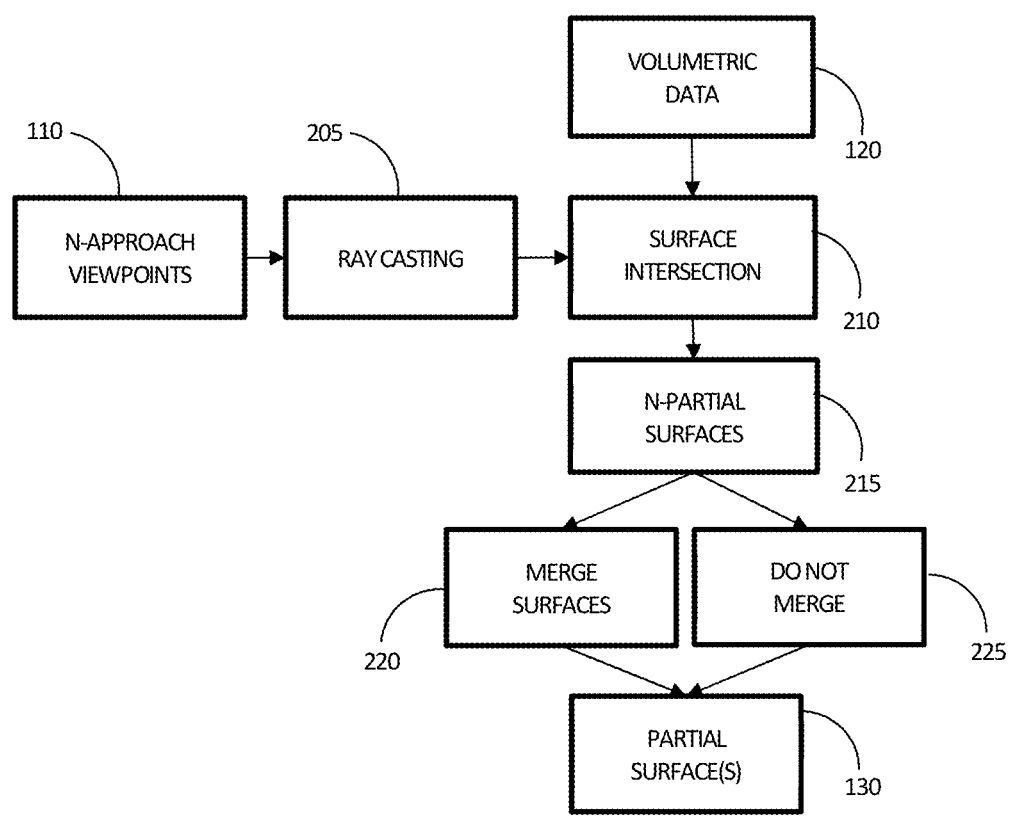
FIG. 7 is a flow chart illustrating a method for generating and merging partial surfaces based on surface intersection criteria.

Referring now to FIG. 7, if multiple approach viewpoints 110 are specified, each set of rays cast 205 associated with each approach 110 is employed to generate an individual partial surface 215. These partial surfaces 215 can be merged 220 to form a single partial surface 130 and/or not merged 225 and outputted to 130. The decision to merge and/or not merge is dependent on how the data will be used subsequently. For example, for display of the surface dataset to a user, it may be beneficial to show the merged partial surface as it less likely to be fragmented and thus the user would be better able to orient themselves to what they are being shown.

Another example when merging is appropriate is when only the approximate approach viewpoint of the surface topology system is known. In this case it is beneficial to merge partial surfaces within this range to ensure sufficient overlap between the partial surface and the acquired surface topology.

As described previously, the individual partial surfaces may be combined by a simple union (addition) of the multiple partial surfaces in the case of point clouds. While this may lead uneven point cloud density in overlap regions this can processed by removing points within a certain specified spatial tolerance of one another. An alternative method is to sample the merged partial surface in a spatially uniform manner.

The use of unmerged datasets may be more appropriate for use in registration algorithms where the approach viewpoint of the surface topology system is known (for example, through the use of position sensors). However, on-the-fly-generation of partial surfaces may be computationally inefficient. In this case, and as described above, the partial surface which is the best match to the approach viewpoint, specified from sensor information, can automatically be selected from a list of pre-generated immerged partial surfaces and used in the registration process.

In other embodiments, independent registration of all partial surfaces 130 from unmerged partial surfaces 225, to surface topology data, can be performed. In one example embodiment, the best partial surface(s) from the set of unmerged partial surfaces can be chosen manually or automatically (for example, based on the registration error, or based on the match between the approach viewpoint corresponding to a given partial surface and the estimated or known approach viewpoint employed during imaging), for registration to surface topology data.

It will be understood that it is not necessary for the surface topology dataset and the partial surface employed for registration to only contain surface information of the same regions of object 1000. In practice, the datasets will not correspond to identical surface areas due to differences in positioning of the surface topology system 170 and or definition of approach viewpoint 110. Generally, the surface topology dataset and the partial surface will have a volumetric coverage that is larger than the region of interest that is to be registered. For optimal registration, the region of interest should be within the boundaries (i.e. field of view) of both the surface topology dataset and the partial surface. Registration accuracy deteriorates as the region of interest crosses this boundary.

Figure 8:
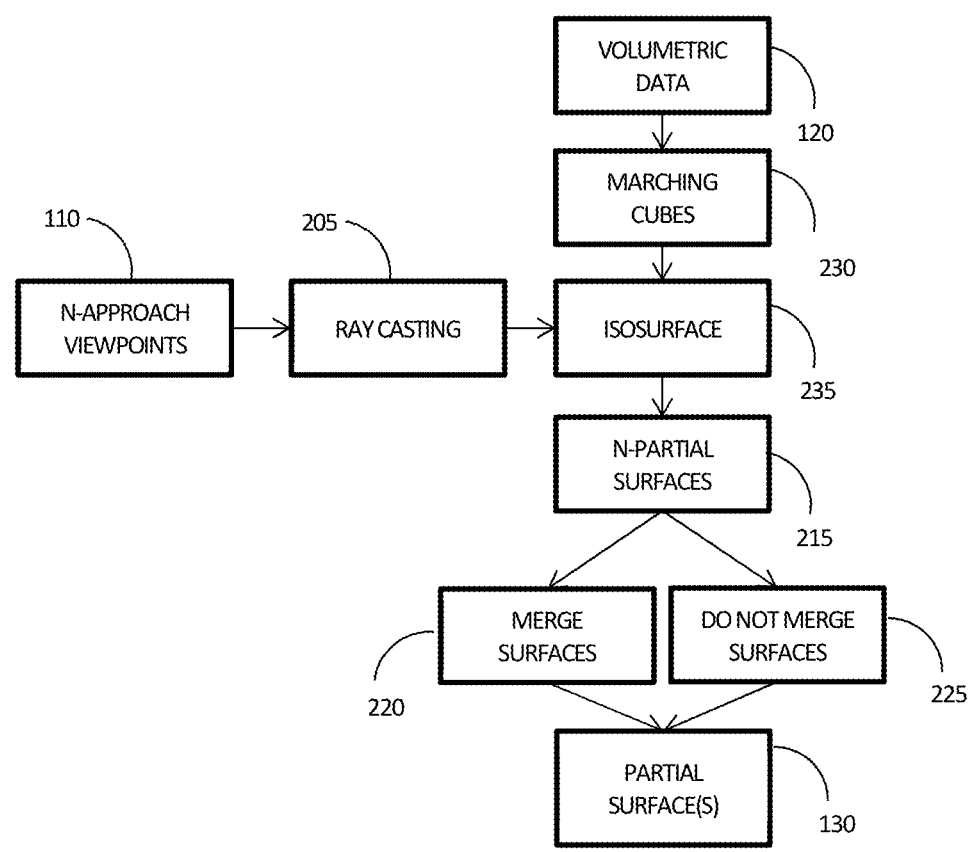
FIG. 8 is a flow chart illustrating an example method for generating and merging partial surfaces based on isosurface generation.

In another example implementation, shown in FIG. 8, volumetric data 120 is first processed using a surface generation technique to generate one or more surfaces. One or more parameters may be used in the surface generation technique to generate multiple isosurfaces corresponding to different structures within the volumetric data 120 which may become exposed during a process or procedure. With reference to the example flow chart shown in FIG. 8, volumetric data 120 is first processed, for example, using a marching cubes surface generation algorithm (shown at step 230). Marching cubes is a well-known algorithm and its variants (marching squares for 2D data) extract an isosurface 235 from a 3D scalar field based on a contour value. It will be understood that the marching cubes method is but one example of a surface extraction method, and that other methods may alternatively be used, such as, edge detection filters and Delaunay triangulation. As shown in FIG. 8, ray casting is employed such that partial surfaces are extracted from the isosurface at step 215, through the use of ray casting 205 generated from one or more approach viewpoints 110. These resulting partial 215 surfaces can then be merged 220 or not be merged 225 for subsequent registration to surface topology data. While this embodiment uses multiple approach viewpoints, the same method of creating an isosurface and then performing ray casting, is also applicable when a single approach viewpoint is specified. In this scenario a single partial surface would be generated.

The potential advantage of using partial surface 130 instead of a full isosurface 235 is that the percentage overlap between the two dataset from different modalities is increased by removal of internal surfaces and restriction of surfaces to those that are or will be visible in the surface topology imaging system.

Other potential advantages of using approach viewpoints to generate partial surfaces includes a reduction in the size of datasets and the avoidance of local minima(s) during the registration process. Furthermore, this approach naturally gives rise to datasets which are very similar to those acquired by structured light scanners, thus these datasets can be placed in data structures called organized point clouds. Such structures can enable highly parallelizable and efficient implementation of search algorithms for normal vector generation, outlier removal and overall registration speed. As used herein, an organized point cloud dataset, as defined by the Point Cloud Library http://www.pointclouds.org/documentation/tutorials/basic_structures.php), refers to a point cloud that resembles an organized image (or matrix) like structure, where the data is split into rows and columns. Examples of such point clouds include data produced by stereo cameras or time-of-flight cameras. An advantage of an organized dataset is that by knowing the relationship between adjacent points (e.g. pixels), nearest neighbor operations are much more efficient, thus speeding up the computation and lowering the costs of certain algorithms.

It will be understood that in alternative embodiments, the one or more partial surfaces can remain as unconnected points, without additional processing using surface mesh generation algorithms and used for registration with surface topology data.

As noted above, although the preceding example embodiments have focused on ray casting as an illustrative method of generating a partial surface, it will be understood that a wide variety of other methods may be employed. For example, alternative methods may be employed to remove the hidden or non-visible surfaces relative to the N-approach viewpoints from the datasets, rather than ray casting. Examples of such alternative methods include, but are not limited to, techniques such as Z-buffering, C-buffering, S-buffering, Sorted Active Edge List, Painters Algorithm, Binary Space Partitioning, Warnock Algorithm, viewing frustum culling, backface culling, contribution culling and occlusion culling.

Figure 9:
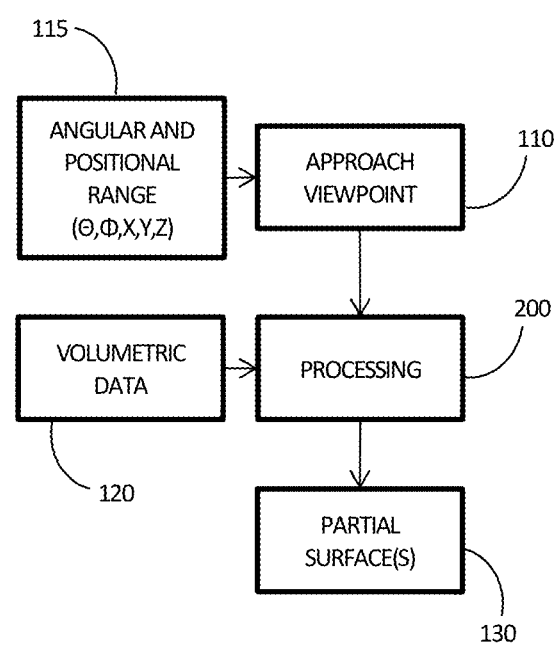
FIG. 9 is a flow chart illustrating an example method for generating multiple approach viewpoints from a single approach viewpoint based on angular and positional ranges.

FIG. 9 provides a flow chart illustrating another embodiment of a method of generating partial surfaces, in which an input angular and positional range 115 is specified in addition to approach viewpoint 110. Angular and positional range 115 specifies a range of variation that the approach viewpoint of surface topology system 120 can have relative to the object of interest. This range of variation may be useful in applications where the position and/or orientation of the surface topology system 120 is not precisely known, such as in the case when h is being manually positioned in the absence of positioning sensors. While specification of large angular and position ranges will increase the amount of surface data and may result in inclusion of surfaces not visible to the surface topology imaging system, it also decreases the likelihood of surfaces captured by surface topology system 170 not being generated in partial surfaces 130.

With the angular and positional range specified, a single user-defined viewpoint can be used to automatically generate a finite set of approach viewpoints which samples the set of all possible approach viewpoints defined by these parameters. These rotations would typically be specified relative to the center/center of mass of the volumetric object or a point of interest on the surface of the object hut more generally could be relative to any point.

The number of approach viewpoints generated may be determined, at least in part, by the accuracy (specified by the angular and positional ranges) to which the provided approach viewpoint in the real space (local) coordinate system is known, the orientation of the object within both the local and virtual coordinate system, and the accuracy of the transform $T_{IN}$. If these parameters are known with a very high degree of accuracy then a single approach viewpoint may suffice (the angular and positional ranges would be very small). For example, in the case of posterior approach spine surgery the cumulative angular and positional accuracy would need to be less than approximately +/−2.5" and +/−5 cm, respectively, where the patient is approximately 100 cm from the surface topology system and the field of view of the surface topology system is at least than 40 cm×40 cm). However, in many situations, these two parameters are only known with much less accuracy as the example given above, thus as the uncertainty in these two parameters increases, so should the number of generated approach viewpoints.

The number of approach viewpoints could also depend on the field of view of the surface topology imaging system, and/or the geometry of the anatomy, to ensure adequate spatial overlap between the set of partial surfaces and the surface generated by the surface topology imaging system.

For example, in cranial procedures, a total of 5 approach viewpoints could be generated to cover the anterior, posterior, left, right and superior surfaces of the head. During surgery, one may choose to merge one or more of the partial surfaces depending on the surgical approach best suited to the intervention.

Figure 10:
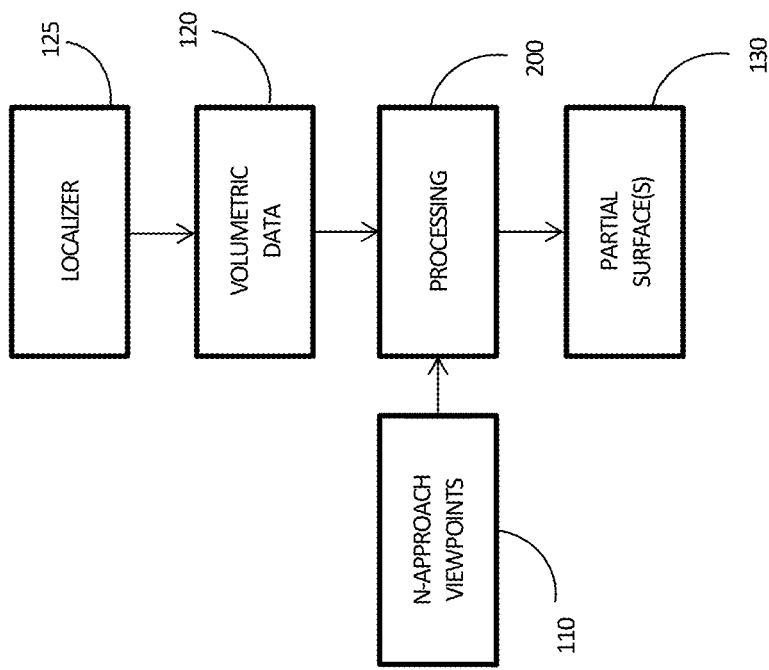
FIG. 10 is a flow chart illustrating an example method for generating a restricted partial surfaces based on the use of a localizer.

In another embodiment, illustrated in the flowchart shown in FIG. 10, a localizer 125, which defines a region of interest, can also be specified to further isolate a sub-volume in volumetric dataset 120 to be processed. For example, the localizer 125 may be implemented through the use of a user interface where the user is tasked with specifying the region of interest. For example, in spine surgery applications, the surgeon would be tasked to specify the vertebral levels of interest through the user interface.

To further clarify various aspects of the current disclosure, an application specific example implementation of the preceding embodiments is now presented. With reference to FIGS. 11-15, flow chart 401 is utilized as part of a structured light based surgical navigation system for spinal surgery as described, for example, in PCT Application No. PCT/CA2011/050257, titled "SYSTEM AND METHODS FOR INTRAOPERATIVE GUIDANCE FEEDBACK. While this example embodiment pertains to posterior (dorsal) approach lumbar spine surgery, it will be understood that this embodiment can be applied to a number of navigated medical interventions and anatomical regions.

Figure 12:
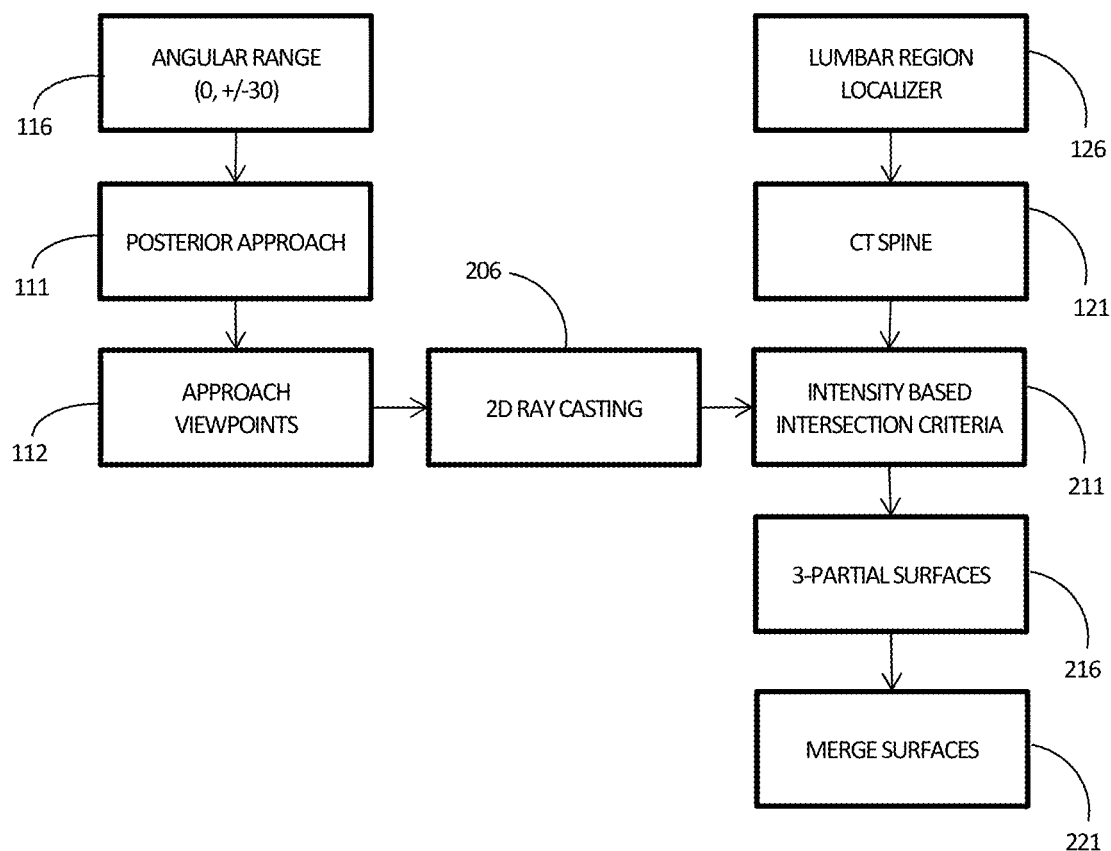
FIG. 12 is a flow chart illustrating an example method for generating partial surface for lumbar region of the spine.

As shown in the FIG. 12, this example method uses employs inputs such as the approach viewpoint, localizer, volumetric dataset and angular and positional range. In this embodiment, the approach viewpoint is specified to be a posterior approach 111 to the spine, and an angular positional range 116 is specified. In the case of a posterior approach spine, in the lumbar region, the angular and positional range 116 may be specified to be 0 (pointing towards the dorsal direction) and +/−30 degrees about the axial direction, which define the typical range of positions the surface topology system may be in during surgery. A set of approach viewpoints can then be computed according to the method illustrated in FIG. 9.

In the present example implementation, a localizer specifies the lumbar region 126. Although in this example a localizer is used, it may not omitted in other implementations. For example, in many navigated spine surgeries, a special CT scan is acquired with a number of unique requirements including: higher slice density, specific Hounsfield units to voxel value mappings (e.g. bone windows), cropping the images with a tight bounding box about the spine or only 1 level above and below the vertebral levels to be operated upon/instrumented. Such a case situation, the localizer could be omitted since the CT scan only encompasses the region of interest.

The example volumetric dataset is a CT dataset 121 of the spine. This dataset could be provided, for example, in DICOM format, along with associated patient orientation data during the scan stored as part of the header information.

The inputs described above can be input into the system a priori using a preoperative planning software or in real-time, via a user interface linked to control and processing unit 10.

FIG. 12 provides a flow chart illustrating, in more detail, an example method of generating the partial surfaces. With the angular range 116 and approach 111 specified, a set of approach viewpoints 112 can be generated. For example, a set of three approach viewpoints may be employed, such as from the bottom, bottom left, and bottom right. These approach viewpoints 112 can be used to generate partial surfaces of the lumbar region of the CT spine data generated from lumbar region localizer 126 and CT Spine data 121 as follows.

In this example implementation, the lumbar region of the CT spine is processed, in a slice by slice manner, using, for example, 2D ray casting 206 and intensity based first hit criteria 211.

Figure 13:
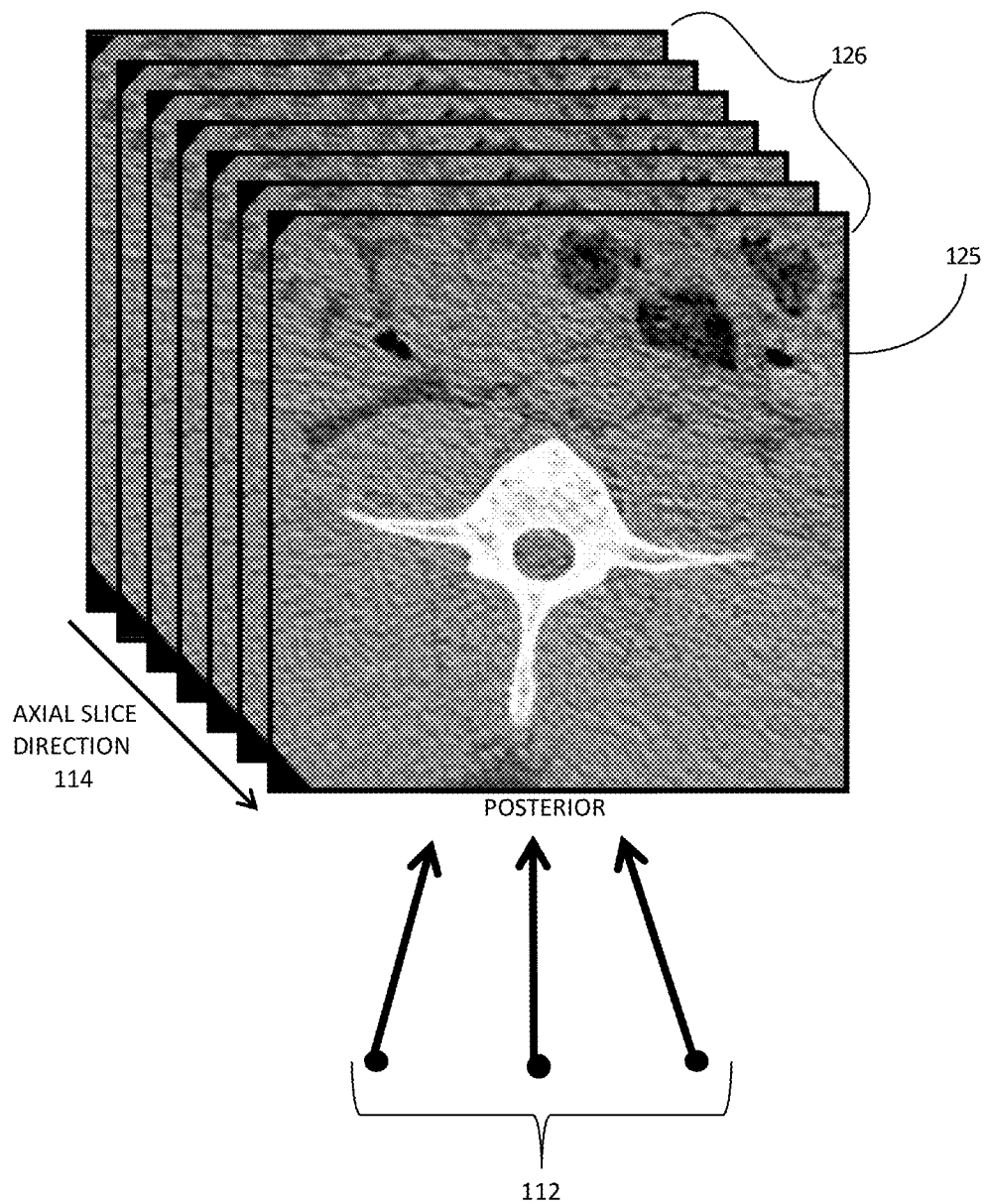
FIG. 13 is an illustration providing a schematic representation of virtual coordinate system of a spine CT scan.

FIG. 13 shows an example of an axial CT image 125 from a volumetric CT spine dataset 121 (depicted schematically). Also defined in this schematic are the posterior side of the patient (known from DICOM header information), the axial slice direction 114 and the 3 generated approach viewpoints 112. Although 2D ray casting proceeds computationally slice by slice, it is equivalent to an orthographic projection from the three approach viewpoints 112 centered on the lumbar region of the CT spine 121 and may be performed in a purely volumetric manner.

For each axial slice in the DICOM dataset, two additional images are generated by rotating the image about its center by +/−30 degrees (angular range). For each image, starting from the posterior end of the image, each column is traversed until the first pixel greater than threshold value (e.g. a value that corresponds to cortical bone) is found. The pixel location is then stored in an image or other data structure for further processing. This procedure is repeated for each of the 3 images. Once each of the 3 slices have been processed, the pixel data from the images that have been rotated by +/−30 degrees undergo the inverse rotation so that all 3 data sets are in the same pixel coordinate system. The rotation of the image by the angular ranges is performed only to simplify ray casting in the image space and is equivalent to rotating the viewpoints.

Figure 14:
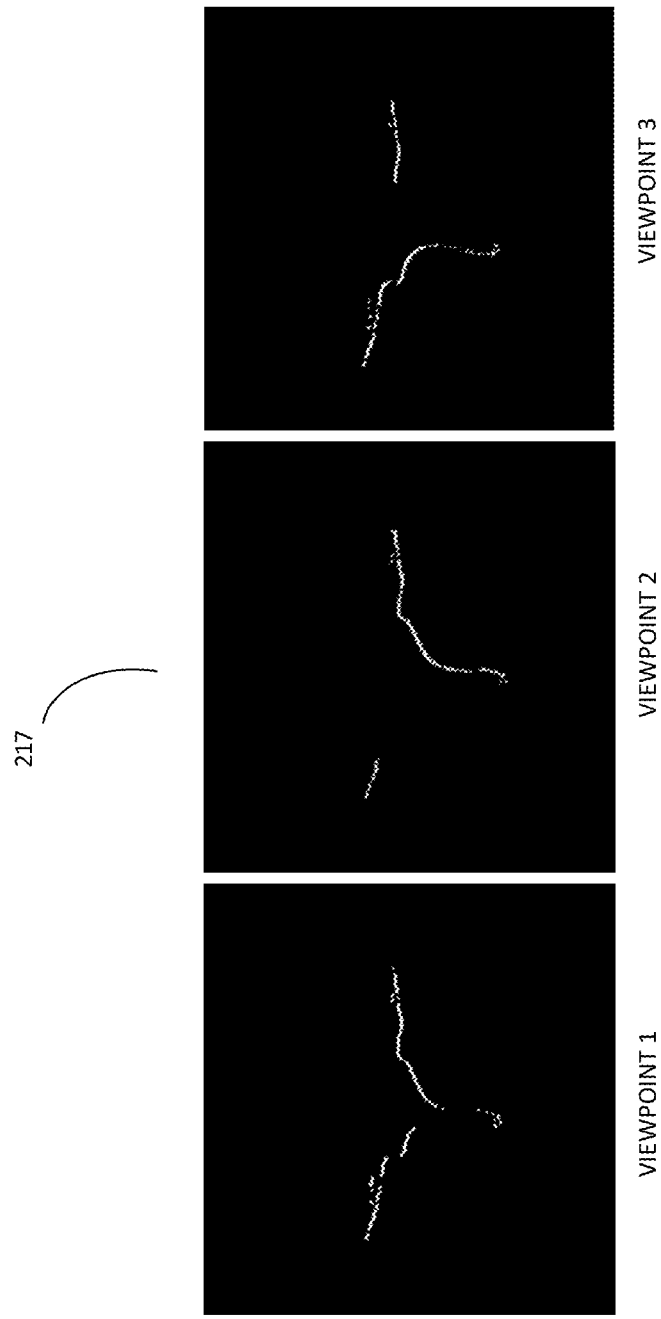
FIG. 14 shows examples of data slices from partial surfaces of the spine generated from multiple approach viewpoints.

FIG. 14 shows example slices 217 of partial surfaces generated using 2D ray casting and intersection criteria on CT spine slice. The three distinct viewpoints generate three distinct partial surfaces, which are then merged through a union (a logical OR operation) of the three partial surfaces slices at 221.

Figure 15:
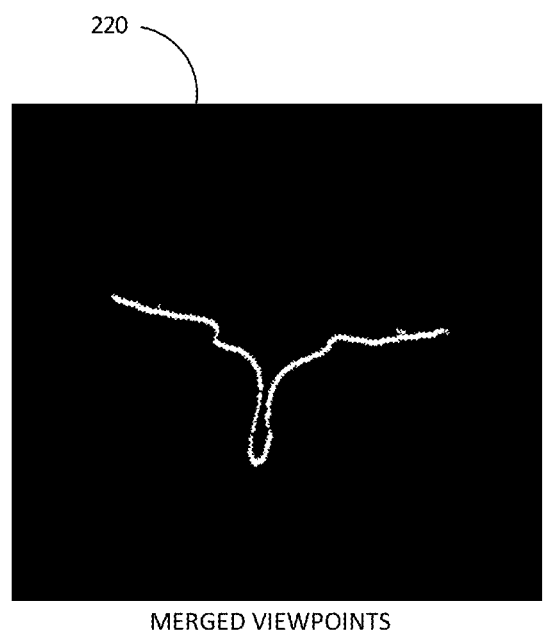
FIG. 15 shows an example of a data slice from a merged partial surface of the spine generated from multiple approach viewpoints.

An example slice of merged data 220 is shown in FIG. 15. The pixel data that is stored in the image shown in FIG. 15 is then turned into position data in the virtual coordinate system based on the information present in the DICOM header, such as the dimensions of the voxels in each image, the slice number of image, and the (x,y,z) position of a corner of the image volume stack.

While the above embodiment only uses rotations about the axial direction of the spine, other rotations about other arbitrary axis may also be used depending on the application and/or positioning of the surface topology system.

Figure 11:
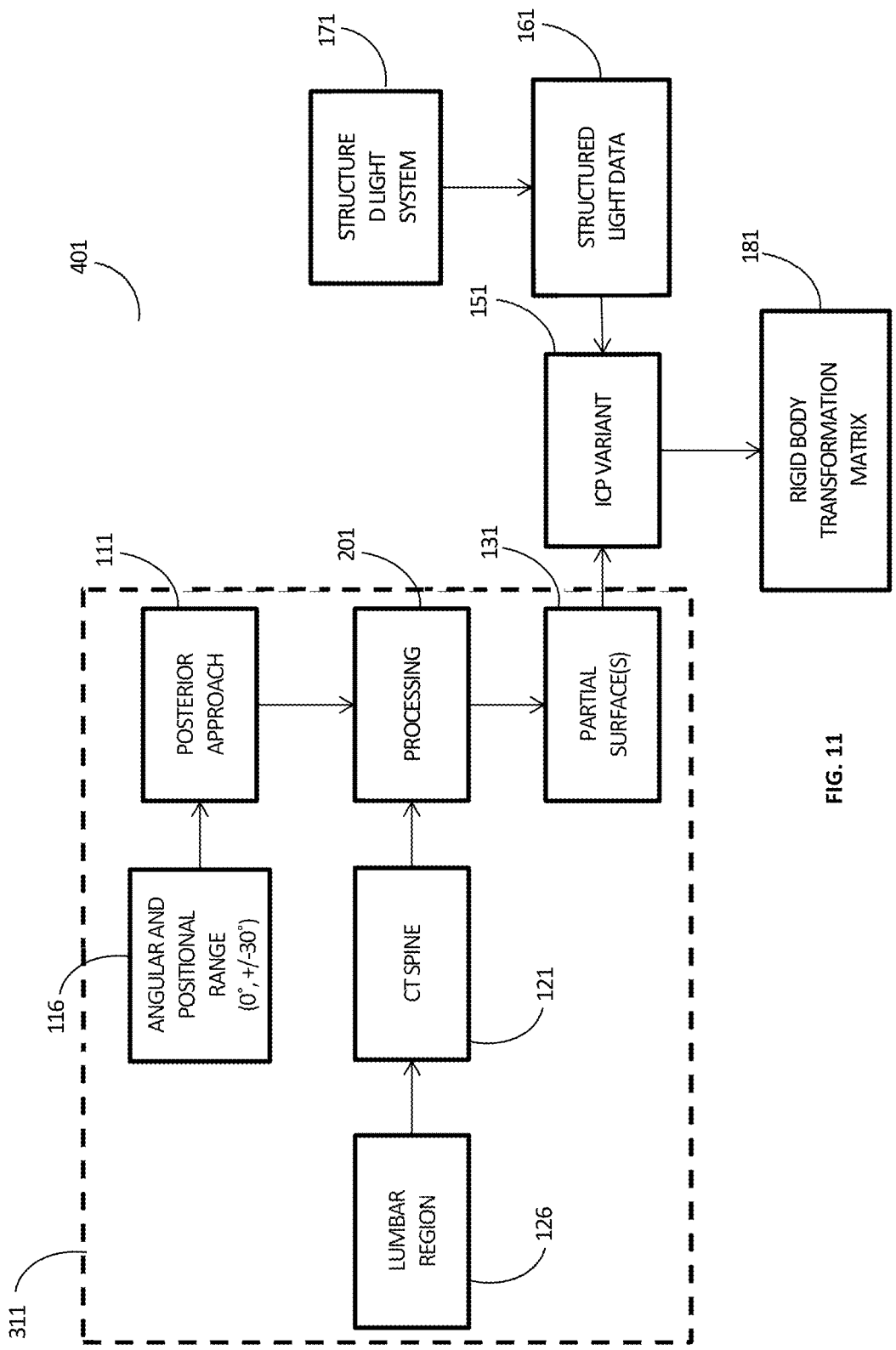
FIG. 11 is a flow chart illustrating an example method of performing partial surface generation and registration to structure light data for posterior approach spine surgery.

Referring again to the example flow chart shown in FIG. 11, surface topology imaging is performed using structured light imaging system 171 to produce structured light data set 161. In the present example, an iterative closest point (ICP) variant is then used to register the surface topology dataset 161 to the one or more partial surfaces 131, generating a rigid body transform. It will be understood that the term ICP represents a wide class of registration algorithms. In general, such algorithms are based on finding the nearest neighbour for each point in two datasets and calculating a cost function for those two points. The cost function could be a simple function, such as the squared distance, or a more complex function. The phrase "ICP variant" refers to one of the many implementations of the ICP class of registration algorithms.

This transformation may be utilized for a variety of purposes and applications. For example, the transformation may be employed by the navigation system or another computing systems to augment the surgical field with patient information from a preoperative scan or planning data. This could be achieved, for example, using active projection directly into the surgical field, or, for example, with the use of a head mounted display. Systems and methods described above may also be used to guide a robotics system for precise surgical interventions. Such procedures may include the use of laser cutting or ablation.

The methods described can also be used to improve the registration of volumetric image data from different medical modalities, such as between CT and MRI. Given orientation information from the image header, corresponding approach viewpoints can be specified in both modalities' virtual coordinate systems. The generated partial surfaces for both modalities will have reduced internal surface structures, which can be useful for registering the surface of objects of interest such as organs. In addition, this permits the use of ICP and its variant for registration problems of this type. Multimodal image registration has wide range of utilities, for example, to correct for deformations caused by imaging at different time points, as well as treatment planning.

Figure 16:
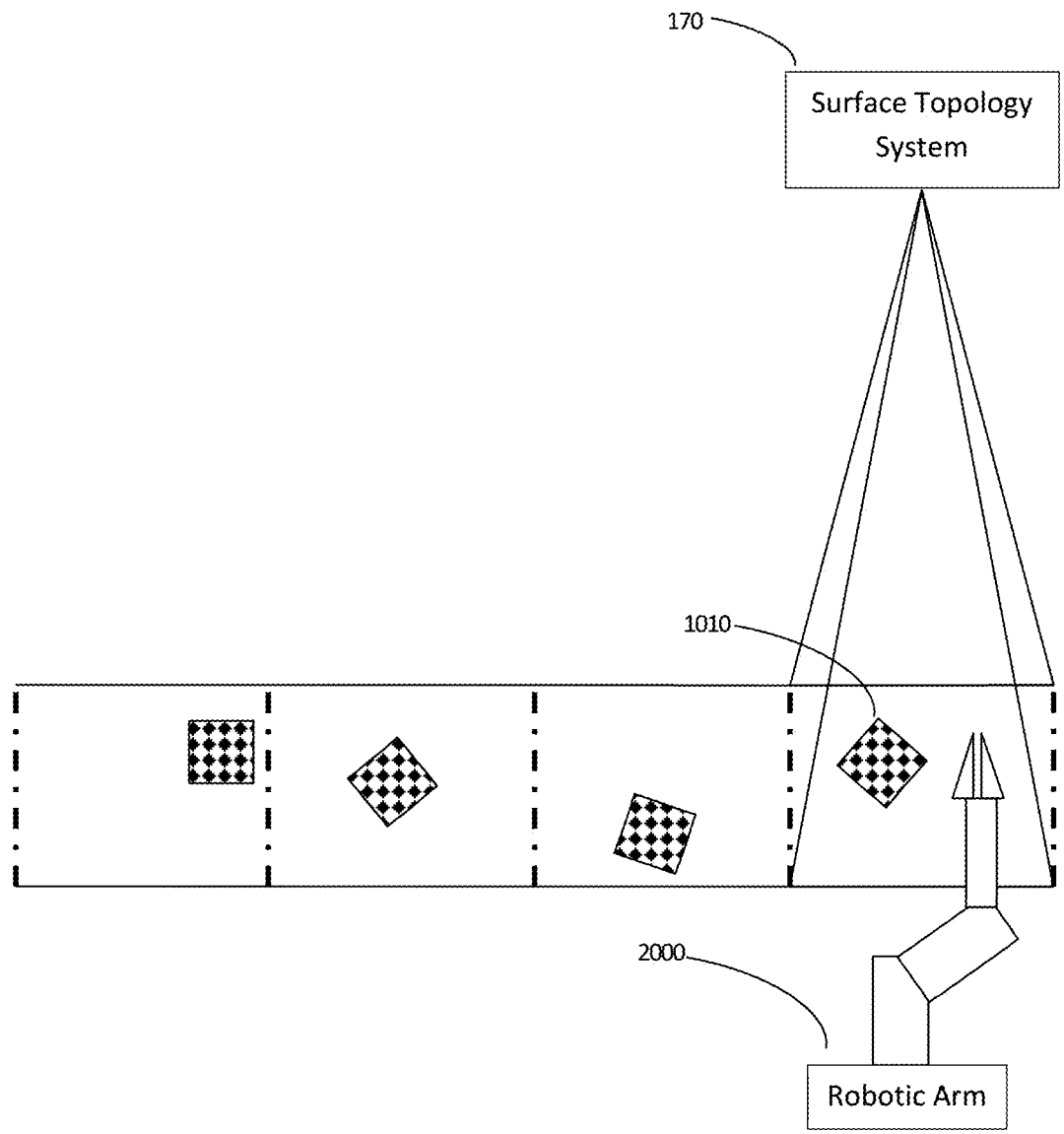
FIG. 16 shows an example of a robotic system using partial surfaces for determining orientation during processing.

In manufacturing applications, the systems and methods described above could be used to orient a robotic system 2000 relative to an object 1010 that may be entering a processing setup, as shown in FIG. 16. Despite changes in the orientation of the object, such as a shift in position, a rotation, and/or a tilt, the preceding methods could be employed to determine the real-time position and orientation of the object, and, for example, rapidly re-orient a robotic or other processing system relative to the object, provided that a particular surface of the object is at least partially visible to surface topology system 170. In these types of applications, the partial surface could be generated from a volumetric representation of the object which could be in the form of a CAD file or similar (STL, SIP, DWG etc). The partial surface would then be registered to the surface acquired by surface topology system 170. Once the registration transform is known, the robotic system could then perform pick and place operations or laser welding or cutting without having to reorient the object. The advantage of using the partial surface is that this process may be performed quickly and continuously during the processing steps which may move and/or reorient the object.

In 3D printing applications a surface topology scanner could be affixed or integrated directly into the printer head or elsewhere inside the 3D printer and scan the region immediately ahead of the printer head to determine if any defects are present via registration to the partial surface. If a print error was detected a corrective action could be taken by modifying the build in real-time. The partial surface in this scenario could be generated from the build file and/or tool paths and/or CAD file which contains sufficient information to generate a partial surface for the particular area of interest at any stage during the printing process. The reduction in data associated with generating a partial surface of the region for registration and determination of printing errors makes it feasible for this process to happen in real-time. In an alternative implementation the scanner could be trailing the printer head assessing defects for correction on the next pass through the region. These embodiments are applicable to all forms of 3D printing technologies, non-limiting examples of which are fused deposition modeling, laser sintering, stereolithography, electron beam free form fabrication, electron beam melting, Digital Light Processing (DLP) and plaster based 3D printing.

In inspection and construction applications, a partial surface could once again be generated based on design files or building schematics. During inspection, building or renovation, a partial surface may be generated and registered to a surface acquired from a surface topology scanner. Once registered, subsurface information (as given in the design files) regarding the object could be displayed via augmented reality (head mounted display, a display or active projection onto the surface). Non-limiting examples of such subsurface information could be the location and size of conduits, wiring, valves, ducts, studs, beams, screws etc.

Partial surface generation could be highly beneficial in scenarios involving object identification where a large database of models exists and must be searched through (using surface registration or a combination of methods including surface registration) for the best possible match. In this application, partial surface generation could be performed based on an approach viewpoint to expedite the search. One non-limiting example of potential scenarios is vehicle type detection in the environment for vehicles equipped with 3D surface topology imaging system, found sometimes in driverless cars. Here, the approach viewpoint can be estimated by the local coordinate system of the car, for example, if the surface topology imaging system is facing in the forward direction, it can be assumed that back of target vehicles will be useful for registration and identification, and hence partial surfaces can be generated from the back of 3D models of target cars from the database.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A method of performing registration between volumetric data associated with an object and surface data associated with the object, the method comprising:
processing the volumetric data to generate a partial surface; and
performing surface registration between the partial surface and the surface data, thereby identifying a transformation between the volumetric data and the surface data;
wherein the partial surface is selected such that surface data hidden when viewing the object from an approach viewpoint is excluded during surface registration.

2. The method according to claim 1 wherein the surface data is obtained by a surface detection device and wherein the approach viewpoint is defined by an orientation of the surface detection device relative to the object.

3. The method according to claim 2 further comprising employing the transformation to generate an augmented reality annotation comprising subsurface information associated with the object.

4. The method according to claim 3 wherein the subsurface information is generated based on processing of the volumetric data.

5. The method according to claim 3 wherein the subsurface information is generated based on a three-dimensional model of the object.

6. The method according to claim 3 wherein said augmented reality annotation is displayed on a head mounted display device.

7. The method according to claim 3 wherein said augmented reality annotation is projected onto the object.

8. The method according to claim 1 further comprising employing the transformation to generate an augmented reality annotation comprising subsurface information associated with the object.

9. The method according to claim 1 wherein the surface data characterizes at least a portion of an anatomical region.

10. The method according to claim 9 wherein the anatomical region comprises a bone surface.

11. The method according to claim 10 wherein the bone surface is associated with one or more spinal levels.

12. The method according to claim 1 wherein the approach viewpoint is determined according to input received from a user.

13. The method according to claim 12 wherein the input is received from the user by:
displaying, on a user interface, a three-dimensional image showing at least a portion of a surface of the object; and
receiving, from the user, the input, wherein the input is indicative of the approach viewpoint relative to the three-dimensional image.

14. The method according to claim 13 wherein the user interface is configured to rotate a camera angle relative to the three-dimensional image, and wherein the input comprises a selected camera angle that is selected by the user, the selected camera angle defining the approach viewpoint.

15. The method according to claim 13 wherein the three-dimensional image is generated based on a three-dimensional model of the object.

16. The method according to claim 15 wherein the three-dimensional model is generated by processing volumetric data associated with the object.

17. A system for performing registration between volumetric data associated with an object and surface data associated with the object, the system comprising:
control and processing circuity comprising at least one processor and associated memory, said memory storing instructions executable by said at least one processor for performing operations comprising:
processing the volumetric data to generate a partial surface; and
performing surface registration between the partial surface and the surface data, thereby identifying a transformation between the volumetric data and the surface data;
the partial surface being generated such that surface data hidden when viewing the object from an approach viewpoint is excluded during surface registration.

18. The system according to claim 17 further comprising a surface detection device operably coupled to said control and processing circuity, said control and processing circuity being further configured such that the surface data is received from said surface detection device and the approach viewpoint is defined by an orientation of said surface detection device relative to the object.

19. The system according to claim 18 further wherein said control and processing circuity is further configured such that the transformation is employed to generate an augmented reality annotation comprising subsurface information associated with the object.

* * * * *